US011458177B2

(12) United States Patent
Yoon et al.

(10) Patent No.: US 11,458,177 B2
(45) Date of Patent: Oct. 4, 2022

(54) ***ENTEROCOCCUS FAECIUM* BACTERIOPHAGE ENT-FAP-4 AND USE FOR INHIBITING *ENTEROCOCCUS FAECIUM* PROLIFERATION OF SAME**

(71) Applicant: Intron Biotechnology, Inc., Gyeonggi-do (KR)

(72) Inventors: Seong Jun Yoon, Seoul (KR); Soo Youn Jun, Seoul (KR); Hyoun Rok Paik, Incheon (KR); Jee Soo Son, Seoul (KR); Sang Hyeon Kang, Seoul (KR)

(73) Assignee: INTRON BIOTECHNOLOGY, INC., Gyeonggi-Do (KR)

( * ) Notice: Subject to any disclaimer, the term of this patent is extended or adjusted under 35 U.S.C. 154(b) by 538 days.

(21) Appl. No.: 16/487,506

(22) PCT Filed: Jan. 11, 2018

(86) PCT No.: PCT/KR2018/000509
§ 371 (c)(1),
(2) Date: Aug. 21, 2019

(87) PCT Pub. No.: WO2018/155812
PCT Pub. Date: Aug. 30, 2018

(65) Prior Publication Data

US 2020/0054700 A1 Feb. 20, 2020

(30) Foreign Application Priority Data

Feb. 22, 2017 (KR) ........................ 10-2017-0023319

(51) Int. Cl.
*A61K 35/76* (2015.01)
*C12N 7/00* (2006.01)

(52) U.S. Cl.
CPC ................ *A61K 35/76* (2013.01); *C12N 7/00* (2013.01); *C12N 2795/10321* (2013.01); *C12N 2795/10332* (2013.01)

(58) Field of Classification Search
CPC ........ A23K 10/16; A23K 30/18; A23K 10/18; A01N 63/40; A01N 63/00; A61K 35/76; C12N 7/00; C12N 2795/10321; C12N 2795/10332; C12N 2795/10111
See application file for complete search history.

(56) References Cited

FOREIGN PATENT DOCUMENTS

| | | | |
|---|---|---|---|
| KR | 20090104427 | A | 10/2009 |
| WO | WO-00/69269 | A1 | 11/2000 |
| WO | WO-2018/155812 | A1 | 8/2018 |

OTHER PUBLICATIONS

Wang, et al., Characterization and complete genome sequence analysis of novel bacteriophage IME-EFm1 infecting Enterococcus faecium, Journal of General Virology (2014), 95, 2565-2575.

(Continued)

*Primary Examiner* — Allison M Fox
*Assistant Examiner* — Qing Xu
(74) *Attorney, Agent, or Firm* — Ballard Spahr LLP

(57) ABSTRACT

The present invention relates to *Siphoviridae* bacteriophage Ent-FAP-4 (accession number KCTC 12854BP), separated from nature, which is capable of specifically killing *Enterococcus faecium* and has a genome expressed by sequence number 1, a pharmaceutical composition, which comprises same as an active ingredient, and a method for preventing or treating diseases, induced by *Enterococcus faecium*, by administering the pharmaceutical composition.

1 Claim, 2 Drawing Sheets

Specification includes a Sequence Listing.

(56) References Cited

OTHER PUBLICATIONS

International Search Report and Written Opinion dated Apr. 26, 2018 by the International Searching Authority for International Application No. PCT/KR2018/000509, filed on Jan. 11, 2018 and published as WO 2018/155812 on Aug. 30, 2018 (Applicant—Intron Biotechnology, Inc.) (Original—8 Pages / Translation 4 pages ).
NCBI, GenBank Accession No. KJ010489.1, "Enterococcus Phage IME-EFml, Complete Genome", Nov. 20, 2014.
NCBI, GenBank Accession No. CP003351.1, "Enterococcus Faecium Aus0004, Complete Genome", Jan. 31, 2014.

【FIG. 1】
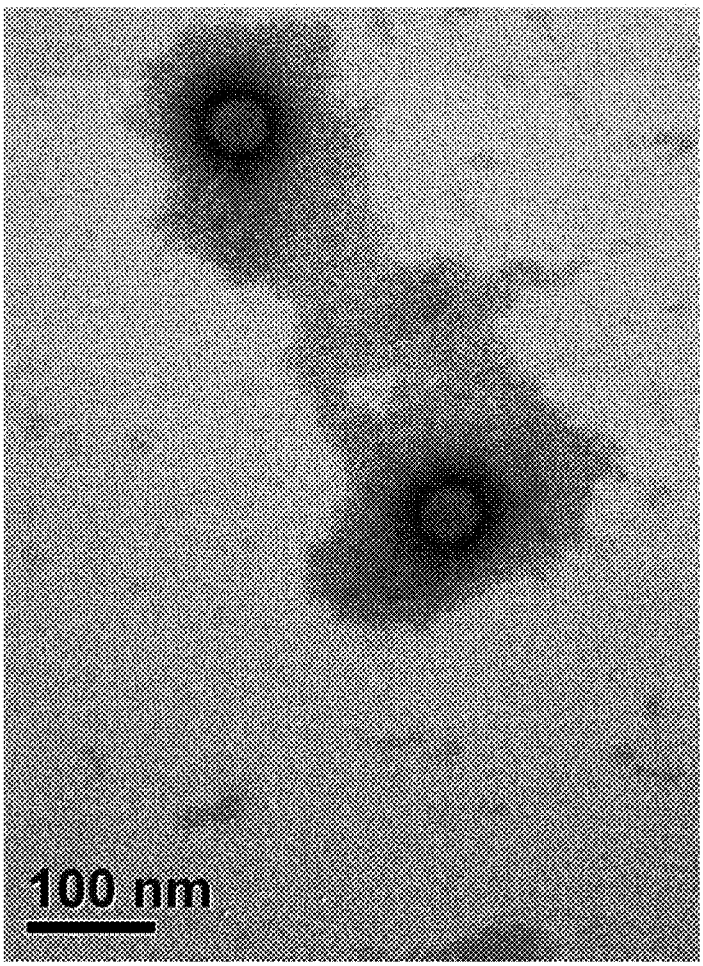

【FIG. 2】
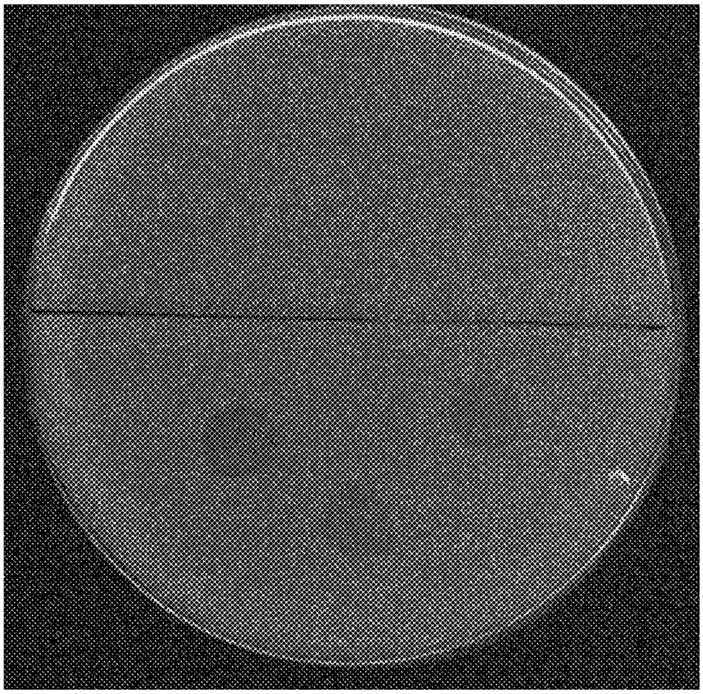

SEQUENCE LISTING

```
<160> NUMBER OF SEQ ID NOS: 1

<210> SEQ ID NO 1
<211> LENGTH: 42407
<212> TYPE: DNA
<213> ORGANISM: Enterococcus faecium bacteriophage Ent-FAP-4

<400> SEQUENCE: 1

agcaatgcca caacggctga tggtttacgt ttaggagctt tatatttaga tgaaatccat      60

gctattgata gttatgacat gttaaacgta cttaaatcat cactagggaa gattccagac     120

gctcgtatat tcattacaac cacagatggt tatacacgtg gtagtgtttt agacagctac     180

aaagaacaag gtagacaagt tttagatggt gaactaggta ttaactaccc taaagatgat     240

ttaaaacaca gtaggctgtt accattcatg tgttgtatca atgatttaag tgaagcaaaa     300

gacgaacaag gttggtataa agccaatcca tcattaaggt ttaataaaca attattacaa     360

caatatagaa aagaagtcat tcaaattgac cgtaatgccg aacttaacat tgagtttcat     420

gttaagcgtg tgaactatcc aaaagaagat aatcgctttg cactggctac acgtgaagaa     480

ttagaagcta ccaaagaaaa atgtttggct gattatgtgg aagaatacgg cgacaatgaa     540

gtttatggtt gtgttgactg gtctaacaca cgagatttaa ccagtgtagg gctaattgca     600

cacgaccaat tacacgaccg ctatttttac gaacatgaaa gctttatcac tcataacgag     660

tacacaaatg gacaaataaa tcctaaagta ctacaagctg gcaaagattc tggtaaatta     720
```

-continued

```
aacgttgttt atacaaaaga tattgaagaa cgttatgtag tagactattt tgtgaaaatg    780
agtgaacgat actatattaa caaaatattt attgaccaat ttaagagtac tttacttaaa    840
ccagcgcttg aaaaagctgg atttgaagtt gttgtagtac cagtaaaaat ggtaactgaa    900
acaatgatcg caccacaaat agataaaatg tttgcacaag gtaatatgtt tgctggtaat    960
gaccccttat ttacgtgggc tatgaacaat ttacaaaaag atattactaa aaatggtgtt   1020
agatttatta aaattgaacc aaaagcacgt aaaacagacc cagccagcgc ttttatctct   1080
ggtttaattg gtttattaga caatgaacca gaccaccaag acggctttat aggtaagttt   1140
attggttaaa tatacattga taagaccttt aaggaggtct tatttttgtg atataatggt   1200
gtgtagtatt atgaaggggg tgcagaatga gtattatttc tgattttcta ggcttttcta   1260
gtgaaatgat gaatgacggc acaggaaaca ttattgattt aaatgatttt tgttataacg   1320
tagaagttgc ttcatatcac agattggcta tagaaatagc aatagattta attggtaatg   1380
ccgttgctag ggttgattgg aatgtattca aaaagaatat tttacaacaa aacatagtaa   1440
caactacgtt aaacggtcaa ccaaacgcat tacaaacatc tagcgagttc tttaagctca   1500
tgacacgcaa attactgtta cgtggtgaag ttcttattgt tgaaattaac aatgaattgt   1560
ttgtagctga ttgttatgaa agcgaacaaa ctaagtataa tgaagtgaca tatagtgata   1620
ttcaaattaa tggtaaagac acacctaaaa agaaatacaa aaacaatgaa gtaatcttca   1680
tgaaatatgg tgatacagtt ctagctgcat acttagaaag ttatatgcaa ttaatgaacc   1740
cattaacaag tagcgctgta gaaagtttca agtcaaaccg tacaaggcgt tttgtgatta   1800
gttctgatga ttatagggct aacttaacag aagtgcaaga aaactttaat aaaatgatgg   1860
aacaacagtt agcttcattc attggctcaa agaaagctac agcaatctat gccaaaccta   1920
aaaagaatga tttgattgat atgtctgata aaaactttat gatgagtaca gacgctagag   1980
gtttaattag tgacacgttt aaaaccgttg caaacgcttt tcatattcca ccagaataca   2040
tgctaggtgg tgcattatct caaatgattg ttgataactt tcttgtaaac gctgtatatc   2100
ctattgttga catgtttaaa gaagcattta acaatttcca atacagccaa ctagaacgac   2160
aaaacggcac tatggttaaa ccagacacaa gtaaatcacg tattgtagac cttaaaacta   2220
ttggtacgtt tattgctcaa gtattcccaa caggagcgct tacactaaac gacattgtaa   2280
ctaaatactt acaattggac gaactaccag aagaaattgg tgacacacgt gttattacta   2340
agaactacag cgaactagaa caatttattg agggtgaaac tcatgatgaa gttctaggtg   2400
aagaagaaac actagagatt gaacaagaag aaaataaaga aactactttg ttttctaatt   2460
ttaagggggt aaaataatgg caactaaact acacattgaa ggcttcattg gtgaagtata   2520
tgactattgg actgatgaac ttaagaacac ttctaacact ggtctggtga aaaacctaga   2580
ggaagcagaa ggtgaccttg aattacacat taattccaaa ggcggtgacg ctttcgaggg   2640
tatggcaatt cttaacacat tgaaaaacta tacagatggc gaaaaagtag ctattgtaga   2700
cggtttttgt gcaagtgctg ctacactacc acttttcgca atggataagg tgaaagcaca   2760
ccccacaaca atgttttgtt ttcataaatc tggcactatg gcgtttggtc atgctacaga   2820
tttacgcaaa gcggctgatg atttagaacg tattgacggc gttgtcactg atttgtacat   2880
gacaaaattc aagggttcac gtgaagaact tgatagcgtt ttagaagaag accgtctcat   2940
gtcagcagaa gaagcgcttt cattaggtct tattgatgaa attattacag aagttgaacc   3000
agaaaaagaa gaaaatgaac cagaaaacaa aactcaacta acattattag gcggttttga   3060
```

-continued actggctaaa gaccatgtaa aagaagaaca tgaaaaatta gaaggttcat ttttagctaa 3120
atttgcaaaa attgaataaa aatattaaga cccctttaat ggggttttaa ttatgctata 3180
ctattaaaag taaagcggtt acacgcttaa tataaagggg gtaacatctt aatggcaatt 3240
aacgaaaata tcactttagc agaagcgtta cgttctggtg aagttgaaaa cgttgaaaag 3300
gctatgacag taatggctaa tcaacaacaa gaaaaaatct tggcaatgac acaagactta 3360
gtaagcgatt ctaaagcatt gaaagaagct tctggtattc aattatcaag taaagaaaaa 3420
caatacttca tggaattgat cggcgaaaac ggcaaagttt ctcctaatgc tcaaaaaact 3480
gtaccaacaa caattattac acgtatcttt gatggactac gtaaagaaca taagctaatt 3540
ggcttagttg accaagctat ggttggacta aacacagaat ggattttttc aattggtgta 3600
aatccagcac aatggggtac aatttgttct aacctacaag aaatcatgga taaaggtttc 3660
cgtaagattg acatgacaat ctttaaactt actgcattca tgccagtatg taaaggttta 3720
cttgacttaa acagccctga atggttggct caatatgtta tcacagtaat tcaagaatca 3780
ttggctacgg ctattgaatt ggcaattatt gatggtactg gtaaatcaca accaatcgga 3840
atgcgtcgtt ctattaagaa caaaacatta gaagaagcta acttattacc agctacagaa 3900
attgaacaat tagacgctga aacagctggg tctattatgg cttcattggt agaatatgaa 3960
gtagaaactg gcgttaaaca aacacgtaca gtaaacccaa gtgacgttgt tattttggta 4020
aatccagtaa cttactggtc taaattattc ccaatgatga cactacaaaa cctaaacggt 4080
gtgtatgttc aatcattacc acttaacttt gaaatcgtac aaagtgaatt tgtaccacaa 4140
gatgagttgg ttgttggggt agctaaagat tacttctttg gaattggtaa aggaactact 4200
ttatcacaat ctgacgaagt acgtttcatt gaagacgaac gtgtttacgc tggtaaattc 4260
tatggaaacg gtacacctaa atttgaagga gcattcaaac gcttcacttt caaagcacca 4320
gcggtaaagt aacaggcgtt actgtagcac ctaaaacagc aagcgtagaa gttggtaaca 4380
cagttaattt aacagcgact gtagcacctt ctaacgctac tgacaaaaca gtgtcctata 4440
agtcaagtgc tgacgctact gcgactgtag acgctaaagg tgttgtcact ggtgtagccg 4500
ctggtgaagc cactattaca gtaacgacaa aagacggcaa taaaacagat actagtgtgg 4560
taacagtaac agaaccagct ggtgaataaa taaaagacac tcttaatgag tgtctttttt 4620
gtgttatact tagttaggct aaacaagggg gtatgattat gagtaatatt tcaccagaag 4680
cgttaaccgc tggtgtaagc gctgtaaaag atgcaatggg tattttattt aataatgatg 4740
ataaaatgat tgaagataaa ctaaatatat ccgcattctg gctgacaaat gaaattttat 4800
atgaaccaga ttttgttatt caaccattaa gcactgaatt aacacttatc tgtgaacgag 4860
ttcgctatga aatgagtaac tcactagaca tttttcaaaa gaactacggt caagacattc 4920
aaaatgtgat aagcagacat gcatataatg attttatgag taaacaaggt ggtgtatagt 4980
atgcctttag atgtagacca gtataatgta aggcgctatt atcgcaacgg ttatatggtg 5040
gttacagaag aaaagtcagt tcgtgaccct caaacaggcg ctttaactgg caaaaccagt 5100
acagaagttt ttagatttaa atataaacaa gcttcattga ctacagcaga tactaaaatg 5160
atgagtacaa acgttataca acgtattact aaaaaagtag aagtaccgta tttagtaaca 5220
tttgaccatg cagaccatgc taaattgatg gtaactattg ataatatgaa atataatatt 5280
gagagagtag aacccacata caacaataga atgtttgtat atttaagttc tgtttctaat 5340
aaaagagagg tgaataatgc ctaatgttac taaacaaaga acgactacaa aaggaagctg 5400
acagacttaa cagtcaaaac atggaacttt taaattcact gcaagaacat tttggtgagg 5460

-continued atattcctat ttatatggac gctgtatcag aagatgaaat acctaatgac aatatgacat 5520
acgttgttat tgaaactggt aattatgata tgacaaaccc acaaagtaaa agtacagttg 5580
atactgtaaa cgtttacttt ttcagcgaag gtagaaacaa cccaacgtat gaccagttgg 5640
caatagtagc gtctggtatt ggtgcaagac tgcactttca aaatgcaaac aaagaaacaa 5700
ttgttcttga tgaaactaat agactaattg gtgtatttgt agctagtttt acaagacaag 5760
tattaaaagg gtgtgtttaa tttggctggt atttatagat tagatataaa tggtaatgca 5820
gaagccgttt tcaaacttaa acaaatgcca aaagatatcg cagacgctgc taataaagaa 5880
cttaaaggcg taactggtat gaaggttatg cgaaacgtta aaacaggtat gccagtatca 5940
aaacgaacta aaacacatat gaaaaccgct gattcactac agctaaaact acaaaaaggt 6000
gtgggttcat atcgtaattt tggggtactt gttgcaccaa ctaaacaata ttggtacatg 6060
aagtttccca ataacggtac tagtacaagt tcaagaaaag gtgctagacg gtttgtacaa 6120
attggtttaa ctaaatctaa gtctttaatt aacgccacta tacaacgtgc tgtgtctaaa 6180
agcacaagaa aaatttaaga cccttaacgt agggtctttt ttatgctata ctattaaaag 6240
taaagcgatt acacgcttat tttaaagggg gtaaactaat ggcagcacaa ccaattttaa 6300
cgattgaccc aacagcaatt gaaacaattg cctttttatt tgaaggtgac gaagaagcaa 6360
tcaaagctga ttgtaatggt tcaatcgcag cagaaacaga aacaacaaca aaaagtaaga 6420
cttgtggcgg tcaagtagtt aaagaaatta cgaaagctac acgtttgacg gtaactatta 6480
ccgctcatat tcctattgag gttttccgcc gtatttatgg tgttaaacaa gatgaacgta 6540
tcaaaccagg tatttactca tacggtaaag cttctaaggg tgaaaagttc gcaatgtcag 6600
cagaacttgt agatgaattt gaggataatt caaaactaat cgctttctta aaactagcaa 6660
gtcaaaacgc gttcacgttt actattgatt ctacagaaga tgaagtggca atggtagaaa 6720
tcgtggctac agcctatgaa gatgatttgg gatattggta tcacgaagca cttgaaagcg 6780
aattaccagc cggcttaact aaagctaaat ggttgactaa tctaacagta gatgacttga 6840
aagtaacacc accagcaaag taacaggggt tactattgca ccaaaaactg ctagtgtggt 6900
agttggtcaa acagtaaccc taacagcaac cgtagcacct acaaatgcag atgacaaaac 6960
agtaacattc acatcaagcg atgatactat tgcgagagtt gatggaagtg gtgtggtaac 7020
tggtgtaaca gctggctcag caacaattac agtaacaaca aaagacggca ataaaacaga 7080
cacaagtgtc gtcacagtga ctgcacaata attaaaacaa aaggggtaaa ataaatgtct 7140
ttagtagaaa tgaaaaaatc aaataaacca acaattaagc ttgtaaatcc agataatgaa 7200
aatgatgtag aagtagtacc agttgaagta aaattgaacc taaaaaaact tcttttcatt 7260
gctcgtgatt atccagaagc taacaaagtg gcaactttac agctaacaca agacggtatg 7320
caaattgata tgattcaatt atacaaactg gtttacgttg catatcgtat gggtaatatg 7380
aatgaatatt atacgtttga acaatttcaa gaaatgtatg actttgatat ggaagaagca 7440
caaagtattt actttagcat gcttaataaa gaatatcgta cagcatactt agaacaaatt 7500
gcacaggcag ccgaaaaagt tcaacgtaca gtaaaagaag accattcaaa gctaaacggc 7560
tgataagacc agaaccagac acagccctag cggttgtgtc ttttctttta gattactatc 7620
acatgtctta tgatatcgta atgagtgatg atttgacttt agaagaatta cttttattat 7680
cagcacataa aactacatgg gaaaattatg taggtctaaa agaaaaggct tatcagcaag 7740
aactagagaa gaaaaataaa aaataggtgg tgaaaacatg gctgacaata caaatgttac 7800

-continued

```
tatacacatt aacggtaaca cgagtggact agataaagct gtggataaag ctacagaaga   7860
ttttgataag ttgcaccagt cagtgaaaaa gacttctgat gaaggtaaca acctaccaag   7920
tattagtaaa aaattagata tgggtaactt gatggaagcc agtgaaagct taagcggtat   7980
tggtgatggt atcattgaaa ttggtactaa atctattgaa gccgctggta aagctcaagc   8040
aatgcaagcc caatttcaac aagtgttcgg tggtctagct ggcgaagctc aaaaatcagt   8100
aaatagtatg gctgaaaaat ttggtatgtt acctaataca gttaagccaa tctttacaca   8160
gtatacttca atgtttaagg gtctaggcat gagtacagaa gacgctatga agaaagctgg   8220
tgacgctacc acaatggcag cagacgcagc agccttttat gataagtcaa tggatgaagc   8280
tagtagtggt ctaaactctt tcattaaagg taactatgaa ggcggtgaaa gtattggact   8340
gtttgccaat gatacacaaa tggcagcgtt tgcagtaagt caaggtgttg taggtgctac   8400
taaagattgg gctagtcttg atgaagcaac aaaacaagct acacgtttgg aatatgccaa   8460
aaacatgcag gaacaagctg gtgctgtcgg acaagctgca cgtgaatcag atggactaga   8520
aaaccaaatg ggaagagcga aacaagctct agaagatttt tatgcgtcaa ttggtaaaga   8580
tatcttacct acgtttatta aactcttaca aggtggtgta acagttatcc aaaatatggc   8640
taaatggtgg ggtcaactcg gtcaaccagt gaaaatattc attgggtcta ttgctggtat   8700
tattgccgca ttaaccacat tagcgcctat tataaccgca attgtaaccg ttgttggtac   8760
gtttggtgct ggtgtgctat taccaatgat tggtattatc gctggtatag cagctgcaat   8820
agctgtagta ataaccgttg tacaaaattg gggtactatt acagattgga tttctgaaaa   8880
gtggtcatct tttgtagact ggttaggtgg tatttgggat tctatcaaag aaacagcttc   8940
caatctttgg gaaggcgtaa aagataaatg gggttcgttt attgattggg tatcagataa   9000
atggaacggt ttgaaagaag ggttttctag cttctggggt ggtcttacag aaggagcttc   9060
caacatctgg caaggagtcc aagagacttg gcaaacattc attgattggg tttcaaatat   9120
ttggaacgga gtcaaagaag tatggtcgat tatttgggca gacattgtag gaattgttca   9180
aataccgtgg acattaataa cgtcattgat tcaagctggt attaatatta tcgtgggtat   9240
ctttgatgta gctggacagt tattaggcgc agcttggcaa gctgtttgga cacctatcag   9300
tgaatttgta agtaccatat ggactactat cacagacttt ctaacaaacg catggaataa   9360
cttagttact acgttacaca ccttctttga ccccattgca gagtggttcg ctggtgtatg   9420
gaacggtatt aaagacgttc taattggcgt atgggacgct atcacaaaca ttgctaccac   9480
atggtggaac aatcttaaaa acaatatcag tattgtttgg aacgctatta aagatgtaac   9540
ctctaatgta tggaacggta ttaaagacgt tctaagtggt gtatggaatg gtatcacaaa   9600
cattgctacc acatggtgga acaatcttaa aaacaatatc agtattgttt ggaacgctat   9660
taaagatgta acctctaatg tatggaatgg tatcaaagac tttctaagtg gcttatggaa   9720
tggtattaaa aatacagcgt ctaacatgtg gaatggtatc aaaactacta tcagtaactt   9780
agtacaaggc gctaaagatt ctatctctaa catctggggt ggactggctg acatggttgg   9840
gggattcttc caaagtgcga aagatagaat agccaatatt tgggaaggtg ttaaagacac   9900
tgtaatgtca ccaattaatt gggttcgtga taaaatctca ggaatttttg ataatttgaa   9960
tatttctata ccacatattc cgttaccaca ttttaaacta agtggtgagt ttaacccact  10020
taaaggtaaa ataccaagtt tagatgttaa ctggtacgct aaaggtgggg tgttcactaa  10080
accaacactt ttaggtggta tgaatggtgt aggtgaagct ggtccagaag ctgtgttacc  10140
tcttagagat aatgttttag ctaaaattgg taatcagatt ttacgagcta ctggtgtaac  10200
```

-continued

```
agcacctaac caagaaacaa atagcactgt aaacaattac aatgtcgtgg ttaacgttga  10260
tggtgaccag tcaacaagct taacagatag agtaacagac agtgttgtaa aaggtattac  10320
taaagtacaa attcgtgaaa gtcgtgcatg gtcataagac actcttaaag agtgtctttt  10380
ttgtgttata ctgattaatg acttaacaag gggtttttta aatgattgat gattgtataa  10440
cagttattat agatggtttt ccagattatt tacacaagtt gtcactggct gaacgtccta  10500
gtattccttc accagaaaga caagtagatg ttacacaagt taaaggtcgc ttaggttctt  10560
tatatcaaca ctattctttt aatgatattg atttcaaatt aacatttaac tacttagaag  10620
aggttgaaga ctatcaagcg ttcaaagaaa agttttatat tattagacaa tggctgtaca  10680
atgctacatg ggtacaattt tcagatgaac ctaatattaa atacattgta aacaatgtaa  10740
gtatttctga cgctgaaaac gatattattg aatatggtag ctttgacgtt gatatcacag  10800
tagcaccttt tggtagagtt gttgaagacg ttcctattgt agttgagaat atagctaatt  10860
ttcaactgtt aaataattct ttacaacgtt catacccaaa attaattgtt acaccaaaaa  10920
caacagactg taatattcta ttaaatggta cacgttttag tttcactggt ttaactgcaa  10980
atagtccaat cactattgat agtcaattaa tgctagttta tgaagaacaa gcagacggtg  11040
atattttaga ccgtagttct aacatgcaaa cattagaatt tccagtatta gaacttgatg  11100
ttaatacgtt tactttgaca aatattagta aaattgaaat ttatagaaat gcaatgaggt  11160
aaggtgagaa aatgagagat attagaacac gcataattac agtttatgat aaaagtgacg  11220
caacaaatat aactaataac gtatataata cacaaggttt aggtgcttta ccagactttt  11280
tagaagctac ggtaaacgct aaactaaacg gtgctttatt ctttaagggt atttaccctc  11340
ttaacggtgt taacagtgaa catttagttg accagaacat tttacaaatg tttgtagatg  11400
aaagtagacc acgacaaaga atgcgtattt atttaactga aacaaatcca attgacaata  11460
caattacagt tgaagcagaa ccaattttca atgatattag acgttctgta gtaaatttat  11520
acgatacggt tacaaccact gttacagcac aacaagcttt taatgcagct aaacaaatgg  11580
ctaaaccaac aatttcacca aattttaaat tcacatcttt agttgatacg ttaacaacgg  11640
ttaagattga gaaagcaaac atgttagaat tttttggggg taaagaaggt tcaatattag  11700
accgctttca cggtgaattt gagaaagata ataacatgtt acgtcatgtt actaggttag  11760
gtactgacca taaaataaag gctatttaca ctaaaaattt aactggcttg aatttagaag  11820
ttgattcaca aagtgtgttg attggtgtat atccttatat ttcagaacaa ggtgaagacc  11880
aaccagaaat cactttacca gaagagtttg tactaacgga atatgccaat gagtttgaga  11940
atggttacat taagtttgtg gactttaaag agaaagcgac tgatattgag actttaagaa  12000
aagctgctaa tgattggctc aaacaaaata taaaaaatca aaaaccaatg gtttctggtg  12060
aaattgaact cgtaccacta aaacaccaac aaggttatga aaaatttgtt caattagaaa  12120
gtgtttcaat gggtgacggt gtagacgtct accacccact attaaatgtt acaatgtcag  12180
ctaggattgt agaatatacc tataatgttt taactaacac atatgaaaaa ctggttgttg  12240
gtgatgttaa aaccaatttc ttagagaaca cagacaataa aattaatgat ttaattaatg  12300
acgctataga cgaacttaag aacggcggtg aaatttctaa tattattaat gatgtggtag  12360
accatcaaac tgacctcatc actggtaacg ctggtggcta tgttctatta gaccctaaag  12420
aaagtccaag tcgtatctta attatggaca cgccagataa gaataccgca aggaatgttt  12480
tacaaatcaa taacgctggt attggtttct ctaaaactgg cattaatgga aagtatgaca  12540
```

-continued

```
ccgcatggac gttagatggc ggattcaatg cctcgtttat tacagctggt gagatagtag  12600
ggattactat tagaggtact acattaatta gtgatggcac tgattataga acaagtattg  12660
ctaatggtaa actgacgtgg tactcaaaaa aagttaacaa agatattatg gagctagaag  12720
cacgtgatta tgtaagtgct gatgccggca ttgtatcata caccatgaaa actggtggtg  12780
gtttcatgat tagaaatcca caggggaact tggtttttag tacgtgggat aatggcaaca  12840
acagaccgtt tttatctttt ggtgcgccaa atttcagata tagtaatgct agttatataa  12900
atgatggtga cggtaattct ttaagcctta atggtagtgc aggtaattca tgggagttta  12960
acgtagctgg caggactatg aaatttacta gagacggtat gctaacgttg ccaggttgtt  13020
tttttggttc atgggaagat gggaaacttg caaggtttga acaatcaacg gtacaagtat  13080
ataaaaattt tactgttaga ggtactaaaa actcaaccgt accgacagaa cattatggac  13140
aacgactatt gaacgcttat gaaactccag aatattattt cgctgattat ggggaagccg  13200
ttacaggtga tgatggtaaa gttcgtgttg atattgaccc catgtttgct gagacagtaa  13260
atctaagtcg atatatgaca catgtgacac ctacagaact agttttgtgt gctgttactc  13320
atgaagatat tgaccatttc atcattgaaa ctagtaagcc aaacgtatta gttagatgga  13380
atttagtggc acaccgtcta gggtatgaag atattagatt aaaagaggat acagcatatg  13440
atagcacagt gcttgaccaa aaacgttttt ttaattaatt aagacactta ttataagtgt  13500
ctttttatgt tatacttatt gagtaaatat tgaagggggt aaaataatgg cgaatagttt  13560
atatacatta gctttagatt ttagtaaaga attaaactac accaaagcta ttatggctcg  13620
tcaaggtgac aaaggaatta cggtgactgt taaaccattt ttaaatggct tgcagatgga  13680
tacgagtggc ggaacattta ctttaaaagg aacaacacca tctaaccgtt atgtagatag  13740
tgttgcaact agcgtaacta gtgaagaagt cacattttct cttgatggca catttatgag  13800
tgaagcagga tattataaac actgctacgt agaatataga aaagacaatc aaattttaac  13860
aacgcaagat atcatttttt tctcactagg agtgtctgac atttcgcaag gtcaagccga  13920
tgaatatgtt tcgcaattag aagagttgat tcgaaagtat aatgaaactt ttgatgcttt  13980
tatggctgaa actaaaggta gagtggatag cttaaatcaa cagattactg atttaactgg  14040
tcaagctaaa acgctacaag acaagttaga tgctctgaaa gaagaaattt ctaagttagg  14100
taacttacaa gtgatgtaca gtaacagcat tgatttcggg ggctatgatt attcggggaa  14160
tccgaatttg atggctaata taaacgctga tagcttctcg caaggtagtg gtgccttatc  14220
tgttgtagat gatggtgacg aggtagtgat tacgcttgat ccaaaccata aattagaggt  14280
attaaaaccg aaaagtcaac cagccctatt aacaggcaaa acatataccg tgagtgtaga  14340
aattatgtta gaaggtgatt tcactggaga ccctagcaag ataggcctaa gatatattaa  14400
aatgcctaac tgggtatcag agctatatac gcgtaataca ttaactgcta ctaagggtgt  14460
atggcaaaaa ctaactggca ccgttaaaat tactgctgcg agtgataacg ctgaaagctg  14520
gcttataatg ctacaaaata aagacgctaa taacagccta tccggcaaac tacgtttgag  14580
acacgctaaa ctcgaagaag gctcaacagc tacaccattc caacctaact tattagcaga  14640
accttacaac atgtgtcgcg aatatcctaa cgaaaatatt gccgatccta cagttaagtt  14700
cccaatcgaa tctggcgacc accaaatata tcaaggttac acagaagaag agcttatgat  14760
aggtcaaacg tatactatca cgcttaaagg aacaaaaccc gcaagtcaaa cctttgtagc  14820
gtataatcat tggactgctc gtttaggaga actaaagccg gttgatgggt tgacagacgt  14880
atggtctcta acattcacac caacgaatgt tgtggcgatg cctaaacttt tccgtgttta  14940
```

```
tcagtatcca cgatcaacag taggcgcatg ccggatcgac tggctcaaga tcgaaaaagg  15000
caacactcga accccgaata ttagtgagta taaatatcgt ggtactggta tgcgtgattc  15060
aaacaatcca aaagattatg tttgggatct agcaccagaa tatgtcgaag ataatttggc  15120
cacagatatt aaaatttctg aaattactgg taaagcaaac aattataccg atgggaaagt  15180
atcgaagatt aattcgcagt tgactgcttc aattaatgaa gttgataaaa aagtaactgc  15240
caatacgaaa tcaataacca caatcaacag cacgctgact gaaatgcaaa aaccagtgaa  15300
atatgaggcg tggtttagcg gtggcactga attgagacca gcaaacgcaa attctagatt  15360
tagagtaagt gaagaaaggt taaccattgg tacaaaacta aatgttgcta tgaatgaaag  15420
tcctttagag tggaatgctg atcgttggga agcaacattt actagagagt gcagtatttt  15480
agttgatgta caaactatgg tagaatttgc tgatcaatgg ggtacgtatg tttatatcaa  15540
catgtggaag gatactaatc aaactcaaac atgggataca ggttacggta tgggtattgc  15600
aagtggctct aacttttggt ttagaactga attgagtgta tctatgtatt gtatgaatgc  15660
taaagttggc gataaatttt caattggttt aggaatggct tctggcaaat cattaacaag  15720
tgcaagaata cacaaattgc atatcatgga actttaataa gacccacata tagaaaaccc  15780
tactatggta taatgtccta gtagggttta aaactatata agggggtaaa ctgttggata  15840
aactggcaca ctatgctagt ttatttaaag actttttaa cgttgctata ggttcagcta  15900
ttctcttact aatcaagaaa attatatcac gattaaaaga gcgaaaagat ttaaataagc  15960
tagttgttca aaatacagaa aaaagatttc aagtcttaga acgtgcaatg attgctatac  16020
aacacgaccg tatttattca cttacagaag aatatttaac acgtggttat gttacattag  16080
atgaacttga caaccttgac tatctttata actcatataa agaacaaggt ggaaacggtt  16140
ctggtgaaag acgttatatg ctcgttcaaa aactaccaat tgtacaagaa ggtgaagaag  16200
atgaaaatta attggaaggt acgtttcaaa aacaagtcat tctggttgac gcttatccca  16260
gctattgggg ttctggcgca agctgttata tatccttttg tgccagatat tgattttact  16320
ggtattaatg cttatttagt tggtattgta aacgctatct ttgcagtatt agctatttta  16380
ggtattgtgt cagatacaac tacacaaggt atttctgaca caccagaaac aatgaaaact  16440
aaaacaccag caatgaataa aaaacaatta gataaaggtg gtaaaaaatg aataaattaa  16500
aatcattctt agttacagca gcgttaacgg cgtcaatgat tttcactggt acagccagcg  16560
cttacacaat tgacactagt cagaagttag cacctaatga aggctccagc caagtagcta  16620
accctaacta cattattttg catgaaaccg ctaacccaaa cgctggtgga ctaaacaatg  16680
ctaaatatat gaaacgtaca tggtataacg cttacacagc ttatatcgtt ggcgagggta  16740
aagcttacca agtaggtgaa gatggttatg tacaatatgg tgctggctcg tatgcaaacg  16800
ctaacgcacc agtacaaatt gagttagacc acaccacaga caaagcaatg tttcaaaaga  16860
actacaaagt atacgttgag ttagcacgtg ataaagctaa aaaatataac attcctttga  16920
cgcttgacac gccttataat caacgtggta ttaagtcaca cttatgggta actcaaaaca  16980
tttggggtga ccactcagac ccatatggtt acttacaaag catgggtatt tctaaacaga  17040
aattagctca tgacttagct aacggttttg gttctgatac aaacaatcca gtaccaaacc  17100
caacaccatc aaacccacaa acagcacatg acaacgctgt cacaaaatct gcaccagtta  17160
ctaacggtaa ttacattggt aaacttgacg tgttcaagga acaaccaaaa ggacaattac  17220
gtattgctgg ttggaatgtg gctgtaaatg gtgctgacgc ttaccgttat ggttttgttt  17280
```

-continued

```
tctacatgga cgctaacact ggtaaagaag tagctcgttc aatgagtaaa ggaattgcta  17340
gaccagatgt ttcaaaagcc tatggtttgc cagttacaaa caaatatgga cttgatacaa  17400
ctgtgcctat gagtaagtta aaaggtcaca aaatcattcc aatgttcaga cgaactaatg  17460
acccaagtgg aaacactaaa ggtggttcac atgatgtaat gttaccaaac atttatatca  17520
atgtacctaa ataaacaaaa gactagccaa ctggctagtc tttttttagt tataagttgt  17580
tcatcttaac tattttaaag tgcttagaat gctcgtgtca acattataaa tagttaaatg  17640
tataaccgcc agttgactta cgtttacctt tacacactgc acatatttta ttagcatgta  17700
aactcaattt acgtgaagct tcatgtattg aattataaat ttcaccatta gaacacacaa  17760
ctttttgat aggtatgtct ttattttgtt cttgttcata ttttgtacac catcttaaat  17820
tgaataaacg attatcatga gtatctctat taatatggtc aactgtatgt tcgtttgatg  17880
attttgggat aaatgaattt agaacacaat agtgtactgt agaggttttt cttttaccat  17940
acttatataa agtaactgta taatatttac cgcttaatgt aggtttaagt attatagaat  18000
ttttaatact atatattcgt cctaaatcag aaactttata taaaccttca taccctttaa  18060
tatcaatcca tatttcttta ttttttgtca tgattaaacc aattagacac agtaaaggca  18120
ataatattat ttgctaggta tagtgtataa gtgaaaaata gaactattac cccatgtcct  18180
tgtaacgctg ttactaacca taaaataata ctcatgatac cttgtgtgaa ccagaaataa  18240
tactgcgctg aaaactggcg gacacataag aaagcaccag taaaaccaat tgtagcactc  18300
aaagcgtcaa taaatggacg tggtgaactt agaacgactg tgtcaagccc atataataaa  18360
gcaaacgtta caatgaaaaa taatagtgtt tgaaatttat gttttgtttg tagtttacgt  18420
gggttaaata ctttccattt acctaagata attggaatat ctaataataa gatatatgct  18480
agttgcatta aaatatcact gtaattacca gtaaccattg ccacataaca cagtagtaac  18540
gctgatacaa aacctagaat accattaatt ggtttacctt ctgtaatagc taacgtacat  18600
gtaaacccta acataccagc aattgtactg gtgaatgata acatgtttaa gccatcctta  18660
aatccaataa ggaataagaa taacaatcca attcccaaaa gaatatagct ttgtttatgc  18720
catcctgtaa attgtttttt ataatattta tatgtgaata gttgagtaat gtgttccatg  18780
tatatatagt tcccctttta attaagattt tttctctaat ggatataatg ttttattgtc  18840
tgtaaactgg cttaactcat gaaaaggcat gtcaccagca caataattat ataaatctaa  18900
accgtattta ttggcgttct tcatattcca tttagcgccg tttagtttag tcaatacata  18960
aactgcttca agagtgttta acgctttaac ttcatgaagc ttgtaaataa tttgtgtgac  19020
tagttctata cggtcttgtt tattattcac ataatcataa caagttacgt ctaaaacaat  19080
tttaggaaag cctaaatctt tatcaatcca tttctgataa ttttcgtgat gtcgtttgaa  19140
gtactcaaat agttcactac cttcttcaac cttttcaaac tctctagcac gtgtattaat  19200
acgtttaatt tcttcttcaa atgtgcagtt taagacaatc attaaatctg gtgttttctt  19260
tggtagtggt tctaactctt ttaacatacg atttaataat ctgtgataga cttgttgttc  19320
aagttcgctt acatgtcctt cttgtaccaa ctggtctaaa aagatagaat cttcaaaaat  19380
agaacggtct aaaataccgt tgttaacact catagcttct tgaatcattt caaagcgttt  19440
acttaacata tcaatctgaa acaacaagcc gtatttttct ttgtctttat aaaataattc  19500
aagcattgga ttttcttcaa ctggttcata tactgcttta gtatttaata agtcagctaa  19560
aatttgggtc atgcttgatt ttcctacgcc tataacgcca gctaatgtaa tcaacaacta  19620
tttacccct aaaatagatt gtaatacgct agggttaaac ccttgtacat atccattata  19680
```

-continued gttatcacta tcaatataag tcactggtac agataaaaat ccagctagtt taatttcacc 19740
tagtgcatgt gtatcttctg tgatatctga atattcataa ttaatattat gttcatctaa 19800
ccaacgtttt accattctgc attgttgaca ctttggtttt ccaaatactc ttacaaattg 19860
catttttatt acccctttaa tgttatttac tacatttata ataatacatt aggggtcaaa 19920
caatgtcaac ccctaaataa actaatcaat ataatttttt actgatggaa actcaaaacc 19980
tttattgcga tattgtgagt gtgcttcatt caatctaaca gcccaatttt caccaaacca 20040
gtttaaaagc aaatattcaa cttcactaat gtagtattct ctatcaattt catcaagttg 20100
gacaccttca ccacaagctt catttgaaat agtatagtat tctggcgctc ttggaatacc 20160
taagatataa gaatcttcac cattcacttc aatatcgttc aaatcatcat caactaacca 20220
tgacggtgtt gtttcgtcca taatgtctaa agaaccacca cgttttactt taaagagttg 20280
tacagctttt gatgggtctt tgatagcaaa cgaacggttt actttttgtg ctggttgttc 20340
agtaccatct ggaaaacgca tgactgtttc atcataagta tagccagttt tagaaatgat 20400
ttggaattgt ctaatctcat cacattcatt aatgaatttt ctataatcat aaccacttat 20460
tacatagttc agaaaagcat tactaataat agcttttgat acttttaaac catgagttaa 20520
accaattgaa ccttttactt taacagaacc attggcttca ataccaacgt aattatttac 20580
gtctctttgg tataaggcta tgaactcatc tttatcaagc gtatagccag tacgttcagc 20640
ccaatcatta gcagcttcat caatttgttt ttcgctctct tcatcaaaag gtaaatagta 20700
atgagcgtct gtgtttgatt ggaaaattgt agcgtgtggt tcaatctttt ctagtaagtc 20760
aaacatagct acttgaccta ctaaacacac aagaagtcgc atgcgtgggt catatagttt 20820
attgaactca gcacccatag caccatactt agtatttaga ggaagtttga aaccatcaat 20880
taatgttttt gttggtactt ctacgccgtt cacgtcaata aattcagcac tttcatattt 20940
ggctctcatt cgttggtcta agatgtcact gtaaacatgt ttcactggtt ctggtatgtt 21000
tctacttaac aaaccgaaca agaccattgt gttaggatat agagaaccta cgtcacgtgc 21060
tataaagcgt ccaatatgaa taaatgactt gatagcacca tgaataccac ccacaccaag 21120
tttttcttct aagtcacgtc tttgtactga tactgaaatt gcagcgtgtc ctttatcgtt 21180
tttatcaaat tcacaaccag tgaaagcgtc taaaacttct ttagtttcta cttgtaagtt 21240
ttctggtaat tcccattctg ctaattcatc acctctattt ggtgcttttt cagcttgtaa 21300
gaccattgct gttaagtttg cattggtttc acctacagcc atcttatcta agccgtacaa 21360
agcacaaaga gttactttag ccagtaacat tttaatgttt tgttcaaaac gtagcttagt 21420
tgctagtacg tcgtttttac agtacttgat attttcttta cgctcttctt ctgtcagttc 21480
tctatcaata tcaaacggta ctgtactttc tctaatatca acacccaaaa atccttgatg 21540
ttctttcagt gagaaccctc tattatccat gtataagtcc attgaaaaca ttggtgttgt 21600
cttattgttg tatttagtcc aaatctcttt accgttctgg ttaacaatgt aatcacttat 21660
ttcaaaaggg tctttacctt gtaattggga tcgcatgaca tgattatcat agtgtgcatt 21720
attataacca atgaataggc tatcacgatt atccagatag aactgtttta aataatttgt 21780
atcgttttct ataatagtcc attcaccagt gaagtaatca agaaacacat acaaattaag 21840
tcttttaaat acttcaatat catagatgaa aatagtttgg ttactagctt tatcattagg 21900
tctgaaatat gggtctatac cctcatcaag ttctagttcg tcaatcactt caaatctgct 21960
aaaaccttta gcaccagtgt gattaatata gaatgtttga ccttcttcaa ggcgttgtac 22020

-continued

```
tttagccatg tctaagtgtc tactatgcat tacatagctt gttgcacgtc taccagtgcc  22080
aatttcttgt aatgtaataa tatccatgtc attgcctttt ttactggttg tactaacacg  22140
actaattaca ataacttctt ttttaccata ttgcattggt tgaaatgctt tagagttacc  22200
agcaagtgtg gcaaacactt ctaataattt tttagctagt ggttttgcat ttgtaaattt  22260
tgctacattt aacattgaat cattcctttc atatttcttt taaagtataa caaaaaaggt  22320
tgactactgt caacctctaa ttttaaatta ttgttttggt aaacggcgtt ttttaagttc  22380
taaataagta ggtacttctg tacttacttt attttcttta acttcaactt tcaatgtttc  22440
accaacaagt ttttcatgtt cttcccattt aacaccagtt aagtcttcaa attgttcttt  22500
cttgtcagcc agtttagact taactggaat tgaaatacct ttagatttaa tatattgacc  22560
aaagttaaat gatacaaagt attcaccttc aagtacttca ccagtatctt catcttcaag  22620
cttttctaac accaaacggc gttgcgtgtc atagtctctt acaccaacaa ctttaccttt  22680
aaattgtaca ccaattagtt caacgtctgg acgtaataat ttcttaactt cccaaaaagt  22740
agcgttgtta ccatttacaa atacagtaac ttctttacct tctaacattt ctaaatcatc  22800
aacagaatca atttcaagat attctttaag tgcttcattg aatttttcta atgtttcatc  22860
attatcaacg aatgttttct tgtctttgtc atagtcacgt gcaaatagat tgattgtata  22920
agcttctgat aagtcttctg gtgctacggt aacgtttaaa acattaccgt caaattctgt  22980
ttctaagata ttcattactt tttgttcgtt tgctgccatt tattaaaacc gccttttcta  23040
ttttatttta ctttattata gtaacatgat ttcgctatga ttgcaagtgc tttttaaact  23100
tttttgtaat taatttgttc taagtttaaa gctcgcattg cttttcata ttcttcttct  23160
gaactaaact ctaatgtaac tgttactggt ttgacttctt taaccactgg tttatcaaaa  23220
ctaaattctg gtacggctga ttgtttacgt gctttctttt cagcttctaa tcgttctgct  23280
tctttaacca tttgttcata ttgttcaatt gcttggctca tgttaaaccc atttgtttta  23340
taatatgcta gaatgttcat acgaacactt tttattggat atttaacttt aagctctgca  23400
taattacttt caaacgattc aaaccaatta ataatagacc gtcttttttc aatttcagaa  23460
catgttttat ttaatgtttt tggaaagttt cgtttgaatg attcaaaatc taaccagcta  23520
ggagcgttgt attcgtccat gtatttatga aacatttcac ctaatgcaat ttcacgttct  23580
aggcgttgct gtgcttcata tgctttgatt tgttggtcta tatgtgtttc accttcatca  23640
agtaaagctt tcaattcttt tactttctca tcaacttcat tataaggttg taatacttgc  23700
tttttaagtt caatgcgttc tttgtcaacc agtgagaatt gttttcgtac ttgtgctaga  23760
agtttttat acgttgttga tgtttcttct gtgactgtta cgtctttcat ttcgtcaact  23820
aattttgtaa tgtcttcctt cattttatcg tacgcaataa atgaaatact tgctggttgt  23880
tgtaattgca ttgttttcgt tgaaatttca aattcattca ttaaatattc tccttatatt  23940
taaatgtata accatacgca gtttttgctg ttcctttagc actacgtgta atagcgcttg  24000
gatattttat tcccataagt ttagcacatt ctttagcact tttatataca ataccagttt  24060
caacacataa tataggttta gatattctgc catttcttgt accatagtta ctattttctt  24120
tagaagttaa ccattctaaa ttttcaacca tattgttttg tttattttcg tctatatgat  24180
ttacttctgg tttgttttgt gggttaggta tgaatgcttg tgctactaat ctgtgtattt  24240
tcatctttt acgataacca ttattatata aatttacata taaataacca tctttatcaa  24300
caatggattt tagtatttta ccatgtgttg tatttcttgg taaactttta actctaccaa  24360
gcgtgctaac ttggtagaga ccttcatagc cttttacatc tttccaacat tctttttcca  24420
```

```
tttctcaaag tcctctattg ttattgtctt atagtgagtt ccatttgaat catttctttt  24480
ctttgcttca ctattcattt tagctactaa accttctggt gttgcgtagg tgcttgattg  24540
atgtagcatt tcagattgtc cttctggttt tagaaactgg tctttaaact cattatattc  24600
accaatttct aaatgtcgtg atgacccatt gttaaataga tcaatcattg aatcgccttt  24660
aatgtgaaca tagtacctaa aaacatcata tctgtaatta ccttctaata gaagtatgtc  24720
aaccagtaaa ccttttttctt ctaagtagtc tttataatga agtgtggtac tcaaatctgt  24780
agcgtaaagt aatacttgac catcatattc aaatatatat ccttgacatt ctacgttatg  24840
ttcattaggt aaagcggtta ttttcaagtc acctatataa aatgtttgaa aatcttcaat  24900
aattactgta ggtttaatgt aaccatgtac ttttattttg tctgaaaccg ctttatttgt  24960
gattattgta gttcttgggt ggtgttcttt cagcttattg taagcggata aattgaggtg  25020
gtcttgatgt tcgtgagtga taaagacaaa agaagctttc tcaaaggctt cttttagtct  25080
tttgtatgaa attcccatat caataagaat atggtatgaa cttgactggc taatgtgtac  25140
agtaataaga acggcattac cagtagaacc agttgcaata atatcatacg tgaatctttg  25200
tatcattcaa agacccccca cactcaaaag taaagccttt atgtggttga ccagtaacca  25260
tgacttccca caaatcgcta gtatgaatat tgtattttac acaagcttca ccatacgtta  25320
tattttcaat aagaacacct tttagtaaaa ccacacatga gttataacca taaacgcttg  25380
gaattacatc aataatattt gttttatagt caaacatctg tgacatacca ttacatatac  25440
cataggtttg gttatatgtt aaacctaatt gaaaagatag gtctgtaatt gtacctactt  25500
taaatgtacc atctgtattt cttaacgaat aaaccaacgc tgaactaggt gaaatattta  25560
cattagctga tgtactaaat gcttttgttg taagcggtct aatattgatt tcatcatttt  25620
caataatagg tctaatgtgt ttaaaatcgt tttcagtaca ttctggattt gtatctaaaa  25680
tatggatagc ttcttttcta gctttttcca tttctaaagt attatgtttc atcatgacac  25740
ccctgtaatt taccctcaaa taatttaaga cgtgtcatgt acatcattgc tttttctaag  25800
tcttgaatac catgtttctt gttataacgt gtcatatatt taaggttatt aattttgtaa  25860
aatcctctca cttcatctgg tgaaaacatt tcttctatgt ggtctaacag ttgtctaccg  25920
tcagccattt cataacgttg tgtatttgaa atttcttcct tactcgtcat tcccattggc  25980
ttcttcttgc tccttctttt cactggctac tgtaataata cgtttaatat cttcattaag  26040
cttgtttgtt gttttgtcaa tatccatttc accagttgta atcaaccatg ctaatgtagt  26100
tagtattaat ttatataaac gtgaagctac ttctgctgtg tcgttggtgt cagccttcac  26160
attaatatca gctgtgtctt ttgcgataac agcgatatat ggtaagtctt tattttctga  26220
ttcttttttc tttttagtaa aaaaatcaaa cattagtttt cacctcattt tttaattccc  26280
attgatagcg gcatttttgt ttagtagaaa ccatgtgtgc ataattcact gatgacatgt  26340
taacattaag ccacatttga atggttgacc agtctgtacc gttatcaatc attttcttaa  26400
cttgcttagc ttttctatat gataaagccc atccatataa tttacgtgct ttacttgatt  26460
tgtatgctat tgtaaacccc catacaccaa tggctaacac tactaacatt tcaattcctt  26520
ctttcttttg ttttattact cttatactat ataatagttt acattatttg tcaacaccgt  26580
tttttatttc tctttttgct tcccctgcgt ccattttttta ggttgtttga aataattttt  26640
gtgttctggt catatcttga ccagtttatt gtttcgtgat tgtcactaac atcattaaac  26700
cagcttgtaa cgactgtact tttgttaata tccatcacaa caattaaatg acaatcagta  26760
```

-continued agttcaccat ttaaaattac tttataaatt ggcttacatt taacggtaat acgtttctta 26820
taaatattag caccgttgtt cttttcttta tgactgtatt caattaaagt gtgttcaagg 26880
tcttctaatg cttgtctgaa cgcttttggg tcataatctg tcacttcatc aataattttg 26940
tctactaagt gtacttgtgt ttttattcta ttattgtttt ctcgtaatgc tctaaatact 27000
tgtttcttga tacatgtaat ttcttctggt gtcatttgtg ttacatgttt ctttttctga 27060
ccaccgcttt tgcgaactac cccaatactg gctttaccct tcattgttca ttctcctttt 27120
taagtcttcc attcttcttt tttctgtttt taacattgaa ttatatataa ggttgaactc 27180
atcattatct aattgagggt tacaagccgt tctgtttata acccttgcaa tatctctcgt 27240
tttgttaata tccataccag aagccagtaa gcgcccaatc atttgagtta aatagatatt 27300 tctacccoct tcaccagcac cagaagccca catttctaag aactcaccca atttgttttt 27360
acggtctatt aaaataccat cacgtttaat tgggtcaaat atagtgttgt aaatttcttc 27420
aaattcttct ttactggctt ttatactggt catgtttaca taccatgcta gacgtttaac 27480
aagtgttaaa cttgcaccag attctaccat tttacgtata acagcgatta gaaagttatt 27540
aggcttattg gtcatgcctt cattccaaag gttacagaac gctcctaagg cgtttaattg 27600
acgtggtttg ttaaagcgtg ggtcaatgtc tttctgatat acgtctaaca accattctgg 27660
tgcatatgct atatagttag gtgagccaga ttcaacttca tagtcaccta caatatgttt 27720
accatctttc atcatgtcaa tgtggcaact atccatcacg acataatgac cgttgtttct 27780
aaagtcaatt tgtgggtact ctggtaagtt agggttgaaa cgtgtcttat accagctatg 27840
aggtagtttc aaatagatat gtttaccacc agtaggtgtt tttactgtat acgtttctgg 27900
taatgattct tgtaactggc ttaacagttt ctgtagtgat tcatacccac ttggttcatc 27960
ttctgtgtga gtatctaaat caagtacaat gatatctgat atttcaccag ttaggacacc 28020
tatattaccg ttatgtgtta atagtgtttt aaggtcttca ccgttaaatg taccatctgt 28080
aaatggtgct ttctggtttt ctaatagtct atgcattttt acaccttgat tataaagctg 28140
tgttattact tgtctatcca atttaattcc tcctaatgtt taatactatt taagtatata 28200
aaaagacctt aacgcttgtc aaggtctttt ttgatattat cctattaaat ttacataatc 28260
gctatgatat ttcacagctt catatttttt attaaatgct acactagcca gtgtagtttt 28320
aaagtctgtt accgtatcaa ttcttgtaat cgttgttctg tatttgtctt gtcgtttatg 28380
tgtaaaaatt atatatctaa ttgaaccata ccaaatttct gtttcaatct gcatattcaa 28440
acccattcac cacacaagct ttaatttcat cttctgatac tgctacatct ggttctttca 28500
cagtttgaat tacagcaata taagggtcat tttgttcacg ttcttctggt gtaaatactt 28560
tagttacaat ccctaaacta tcctttggta aatttagttc tggaatatct ttggttagaa 28620
tcacatattg tttttctgat aatttcattt attttctacc ccttctacaa tctttttata 28680
tttttcatat gaatcattta atttcatgtt tactttccaa gcggtcttta gttcttgttt 28740
ttgctggtaa ataatatcat tttgtttatt tattttgtct gttaatgata aacctaatac 28800
tacaataata ccaactaaac ttataacagt cattaatagt gtttttattt ggatatttag 28860
gtaaccagtt ttttcttctg gtgcttgctg tatatgataa gttagaaatg aagacgtacc 28920
aacttcttcc gctgatacca attccaatga taatacacaa agaaaatctt tatcatggtg 28980
tttaacaata tcagtagctg cttttggatt tttagcgcat acatatacta tgtgagtttg 29040
ttccatatct atgaaatcat caaagtattg gtaattgatt ttataaaatc gttttggcat 29100
tactctaccc ctttttgaga ccagtcaata aacttcacaa taccgtataa cattataaat 29160

-continued

```
ccaattccga aaataattaa gttgttcatg tgattacccc ttttctttta ttaagtatag  29220
tattataata caaaagggat tgactaatgt caacccctaa tttttattta ttcaaaaaac  29280
tttgtaactg tttcttcaat acgtttttca cttgcttcaa tatgttctag gtcaatttca  29340
atatcactta catagtcagc cacattttct agtaggtcag ccagtgcata gagtgtttct  29400
gaatctggtt tcttaccatt taatagtaat gctttaccag atactgtgat tgtgatttct  29460
ggttgttcca tattattcac catcactgtc tttttcaatg tcaatcaatg tatctaatgt  29520
atctgttaat acttcataat ggttgttgac cgttgcaaaa ttttcagaaa caataatacc  29580
taaaatttga gtacggtctg cgttaactgt accaccttct acaagttcat caaggtcaat  29640
accatcagta gctttttga caatttcata accaatttca tttacttctt caaatttttg  29700
taatagttcg tgtgctagtt cgttaaatgt ttttttcaat taaatcattc cttttatttt  29760
atttaataca ctaattattt tataataatt caagctggtt gtcaacaact ttttcaaatc  29820
tatcttgaat gtatttttta gtgaagtgtt ctgtatacgt ccatttaccg ttgtcacatt  29880
cacagcgata ataaacagtc tttttatctt tctgctttac gtggtcaaac agttcaagct  29940
tttttactgg tttaatatat aaatgaattg tctcatgttt ataccactga tgtaatttaa  30000
tagtcattta tttagaaact cctttcattt cttttcgcgt ttgttggtgt taattgtaat  30060
tgatattaag gtaacaggta cgataacaaa taagccaatt gcaatgccag taaacaatct  30120
aataatcatg tgatagggta gtaaagtaat tagatacgct acaaacgcac ccagccagta  30180
tatagaaatt gctttgacat tgtaacgtgt taaccgtact aaagttttta aaaacattta  30240
tttcacttcc ttttctagta tagatatagt ttaatgcatt tttccttgtt ttgcaagagt  30300
taatttttct gcttcatatt gtttggctgc ttcatgtgtt ttgaaactta aacatactgg  30360
tcttggtttt aaaaaatcat aataagtata tacattatat aaaccgtttt ctttcttgat  30420
aattgtttcc atgtttcacc cccacacaag tatagaacaa aaaatcccat ttgtaaatat  30480
acaaatgaga cttttataaa atgtatttaa ttagatagga gttaggttat atgaaacact  30540
ttatttttgt ctacgaactc atgataatca atacgaaaat taatgagaga gacaaacagg  30600
cggtaaagga attgaaccct tcttataggt tttggagacc taattttcac catgacaccg  30660
ccttttataa aaaccaccta gctagtatac agaccactta actaggtggg aaaaggaaaa  30720
gaaagaaata aatgaaataa acgaacaact agcctatctc actaactgtt aacagtatat  30780
catatgaaag accccaatta taggggtctt attttatttc ttaaatttct ttgattgtga  30840
tattatcaag acctaataca gctaaagcca gttgtaaagc ttctttgttg tcgtactgag  30900
tagcttcttc taatgtatct gcataggcta agtagtcacc attataaatt tctatatagt  30960
caccatcagt atcaattaag acatattgtg gttttgattt ttcatcaatc acttcaaagg  31020
tatcattttc aacccaaaat gtcatttcac aatttaaatc agtatcaata ccacgacatt  31080
tatatgtgta gtaggtatca ctttcatcaa cttcaacaat tgtaacaata ctaccaagac  31140
caaatgtaga acactcatta gtaattttga gtttagttcc tagtggtaaa aaatcaggct  31200
gtttttcatc ttcaattact tcaaatgtat tttgttgaat ccatccacat ttattatcat  31260
ttctagcata gtagggtaat actgtgttat ggtcataatc aacactttca attgttgcaa  31320
tatcaccttt aataaatggt aaatctgttt ctttaaattt aattttagta tattctgtta  31380
caagtttttc accaacttct tctaattctt ctggtctaaa gttttctcta tgaccatctg  31440
caaatctaag ttcatgtgtg aaaatcacgt tagtggtatg aatatttact aattcaccaa  31500
```

-continued

```
tttcacctct gttaactgtt aacccagcat tatctttcac tttatacatt tttccaattt  31560
ccatttaata tcattccttt tcttttattt aatacagtat tagtatatat gaagggttga  31620
caagtttcaa ccctattttt ttaatttctt gtaataaatc ttttaagttt tcataagctt  31680
cttctgataa gtccataaaa ttaccatcta taattacttg ataattccaa atattactca  31740
aaccccaaat catctttcat tgtttttagc gcttcttctg tttcagccag tgtttcttct  31800
aggtcttctt tacgtgtttc tagtgtgttt aattcagatt ttaagcgttt aatgaaatta  31860
attttgtcag ccagttcagt gattgcttca tctgttagct ctggcttttg ttctgttgtt  31920
tgctctggtt cacgccatac tgctttgatg tgttctttat aaactacttg ttctaattcg  31980
cctacgttaa atttactcat ttaatatcat tccttttctg ttatttaata ctttttttagt  32040
ataattaatt agtgtttgtc aaccagttta taaagtttaa cctatcatca ctccttcaaa  32100
ataatgtagt ccaaactaaa ctaaatacaa caccaaaaat cactatacta aagaatatta  32160
gcattacagc agtttcacca atcatatttt ttaatatttc tatgataaaa gctagtataa  32220
aaatgccaat aaatattaat attgtgacca gtaaacattt tataagttta attagcatta  32280
tttcacctct cattttattc ttaatgtagc ttctttacag tcaataattt tatagtgttt  32340
cttgggatat gtcaacctaa attcgttgat agcttccctc attgtttcag ctaggtaggt  32400
taactggtag ttctgaccgt tacgcctagc cagtatgaca aaagttgtca ttgtttcact  32460
ccttacttgt aaatgtccat cagtgtaata attttctgaa ataactctgc gtctttagtg  32520
agaaaatgaa agcgttcttg gtgcaacttg tctttccaat gaaagcgctt ttctagctcg  32580
tttaactctt caataataac cctcatttct ttttcacact gttctatttt gttgtgtgtt  32640
tgccaatacc tttgggtggt gtggctttgc atattgtctg gttggttcat ttgtataagt  32700
ctcttcattg ccttatcatg agacttagag agtcgtttaa actctctaag ttgtattttc  32760
atgatatcgg tgtaatactt ggctagcact ctaataacat ctcttttagt ttaaagtagt  32820
cacttctaag ttcagctaga accttttcat catctgtatt cgcccatttg aaaatatcgt  32880
ccatttggtt gtctacccat tctgaaactt ttgcaatgtc ttcatctgtt tcaatgtcag  32940
cagctacatc aacaaagtcg ctgtaaagct tatccatttt cttttgtagt tctttgtatt  33000
tttcgtgtgt cattgttgtc attgttgttt cctcctaaag tttaatttgg ttggtactcg  33060
ttcaccttac ggcttaaccc tcaaccttat gtactaagta taccacccac atggagtggc  33120
gtacttagaa aagcattatg ttttaattaa aaaattctaa tatatgatat gaaccgtagt  33180
acaagtaaaa atctttaggt actcctatac cttccaccat tatcccatat ttgtcttgtt  33240
tggtgacagt agcaataaat gttttcttag aagcgtggtg agctatatgg attgttttac  33300
ctaataattg tgacctttct tgttgctgtc ttataaactc atcttttgac actaacattt  33360
attttcctcc tctttatctt atgaattaag tatacaacaa aaaagtctaa ctgtactgtg  33420
aatacaatta gacttttatt aaagttttct aatctttctt tctaatacct attaaacatc  33480
tagtgcttac agtagtacca ttttttagtc tgatacgtgc tggtttaaat tctacaccag  33540
cgtcttgtaa acgttttttc atgtttatcc atttcacatt ggcttcactt tcatctttcc  33600
acgcttcaaa catccctttg acgtcaactt gttctatacg gtcgttaggg tcttttgtta  33660
actctaattc gttatcattc aagaaaatct ttgtaatgtc gttgttgtct acataggtgt  33720
ttgtcatttc tttagccagt tctgacttgt agaatgggtt tacttgacca gacaactcat  33780
catctaaaag aatgtctcta catgcttgta aacaattcca tacaaattta ccaatgattt  33840
caccatcata atcttcacgc tctttacgtt ggctgttaaa atgtttcatt tctttttcgt  33900
```

-continued

```
gtttaccgtc tttaaattct tttgtaaacg gtactacaat taaacgtcta accataccaa  33960
atgaattatc tgaaaactta ggtagtttat ttgtagaaaa taatagcttt gcatagttga  34020
caaattgaaa tgggtctttt cctttacgtt ctgcttgtat catgtcttta ccagtgagag  34080
atttaagcac accagtatct tctaaatatt ctgcaccact atcagcgtca atatttgcta  34140
atttgtgttg taactggctt gatgagaagc gttcattctt tgttgatagt ttttccaatt  34200
gtacactaga aacgtttttg cgtccaccta aaacatgtgt aatgtagttt agcacttgtg  34260
atttaccatt agcaccactt gactttctag ggtcgtttac aaaatatgta aacattgcat  34320
atttgtattc tctatagaaa caatagccta ttaattgcat gatggttttt aagctatctt  34380
ctaccaccca ttctagccag tcttctacaa ttgtacgttc gtttgtagga actaagttgt  34440
aaggtaattg gatagtgtgg tagtcatcta tttggggttc tactattgta tttgtttcaa  34500
aatcataagc gccgtttttg aatagtattt tatttggatt tggttcactg ttgataagtg  34560
tttcttcacc ttcaagtttc ttcattgttg ccaattcttg tgataagcgt tttctttcat  34620
agtatacttg attactggca aggctttctt gataaaacca ttgttctagg tagtatctat  34680
ctatatgagc tgataaaggc gctgtgattc ccttccatag accagtgttt tcattgtatt  34740
catagggaat acctagtgag gggtgggcta tgattggaat gtcatttata aagttttcta  34800
cggcttgttg ggctttaatt ccaatggggt atatgttccc ttctttgtct tctttatatg  34860
atactgattg ttctactttt gcacgtgttg aaatagcttg ctgggcttgt tgggttgcta  34920
actctttagc tagtgcttgt tgttctggtg tagcgtcttg tactttatct tctggaaggt  34980
caaccagttc aaaattgttt tccacgtata tcactccttt tatttttaca ttagccagtg  35040
taacacatta attttataaa aacaataggt ctaaccagtg tttacagttt ttgttgacac  35100
tgtttacact tttgtataca gttttcaaaa aaagtgtaaa cacctaaacc attgatatat  35160
aagggtttta cctactttgt ttacaatgtt tacaataatt atatatttaa ataaataata  35220
tatataatat atagggggtg tatacagaaa tatgatactg gctgagatag aaatagaagt  35280
gacaaaaact gtaaacatgt aaacaaaatc gctgtaaccc ttgataatac tggcttttac  35340
cctaacaaaa ctgtaaacaa attgtttaca aaaaatgtaa acaagtgaca aattttgaca  35400
acactagcta attaacaccc taaatcgtgt ttacaaagta tgctatactg gttcatgagg  35460
tgaaaataat gaaagaaagt aaattccaag aacaagtatt agatcattta gaaaaaaagg  35520
gtgcatggtg tttcactagt catggtgggt ctatgtttca agttgctggc ttacctgaca  35580
ttataggagt atataaaggt atctttttag ggtttgaact taagactggc aactatcaag  35640
ctacacagtt acaaaaatca aagctaaata atattcaaga agctggcggt gttggtctaa  35700
tcattcgtga tacactggtt gacattgata acgtattaga ttatattgat aaaaacggaa  35760
aagcaccaaa acaagaaaaa tatgcattag atatggacgt gattatagat tgattgaaac  35820
attaatactt attttattag gtggcgcttt tgtctttcta cctgtagcaa taattgtaat  35880
tctatttata gctgtttggg ggtggaaacc tcatgattga attattcgac tatcaagaag  35940
agcaagtaaa acatgcctta tctggtaaat ctaggttaaa tttatcagaa gtgggaactg  36000
gtaaaacata tgtagggtta gaaatatata aacgttctaa attcaaaaaa ctacttatta  36060
tatgcttagc tgttaaagtg tctgatttcg tgtctgacgg ttctaatgta gggttgcata  36120
taaacgcctt aaatggtaca ccaacgaagc gtagcgaggt tctgacggct tctgacaacg  36180
tttctataag ctttgaaagc gtttggcgta caccagaact tttaaattgg gttgatagtg  36240
```

-continued

```
atacaatgat acttgtggac gaaagtcaca agttgaaaag tcgtggtagt aaggtagcac  36300
tgtttgtaga acaattagct agtaacgctg gtctagttta tcaaatgacg gcttcaccac  36360
tggcttctgg tcattatgaa gactattacc aacaactagt tatagctggt atttggaaag  36420
aagggtggaa agcctttaaa gaacgctata ttattgaaga attagatagc gtaaaagttg  36480
gcggcggtaa aactcgctcc ttctggtcta ttgttggtta taagaacgta gaagagcttg  36540
aacaactggt taaaagtaat tcagtagcta aaaaacgaga tattgcaagt gaattgatac  36600
cagaagatat tttttactat aataagaagc ctactatgta taaaaagctt gaaaaagata  36660
gagtgttaca attatctgat ggaactatta aagaatatga tagtacaagc ttaatgtttt  36720
ctgctaaacg tcaattatgt agtggggttt taaaaggcat tgataaagta atgaataaag  36780
gtaaattaga tagattagct tcaattttag aagaaaatga aaatgagcgt gttgtaattt  36840
tctataatta tcaagctgaa ctattagcac ttaaagaact cgttaaaaaa gagaaaagac  36900
ctctctcaga atttaacggt caaaaacatg accttagaaa tttcaagaat aaagaaaacg  36960
gtgttgtact ggttcaatat aaatctggtt caactggtct gaatgatttt gtattatctc  37020
atgtatgtat attctttagt tcaccagatt caagtactac ttacattcaa gctaaaggaa  37080
gactgaacag aactggtcaa actaagaaac ctatattcta tcatctaata tgcagtaatt  37140
cagttgaaag taaactgttt gagggtgtat tagaaggtaa agatattaat gataatctta  37200
ttgaagacct tgtgaaatac taatattatt ttgtgaaata taggttatat acaatgtata  37260
aacattgata tatagccttt tttattttat acatttcaca aactcaattg tattattcac  37320
aatcttttat acattatttt gttgtataaa atatacaatg ttcgtattat tgtatatagt  37380
atacattgta tatatgcata ataaaagtta tccacaggta aaatgagggt gggtgtattt  37440
aatatgggtt atttaattat aggtactgtt atttgtgatg gtactataat ttataggtgg  37500
tatagttatt tgtaggtggt atatattttg aggggtagta tattttatac aggactatta  37560
aacaaagccc atcatatcaa tggatatggg tatacattgt attgtatatt agcatggtat  37620
atgtatatca gtatatgtat ataggattgg tctaatatgt aaacgattac atactattaa  37680
tatgtaagac aactatataa gtatgttcta atcttattct aatctaacta atcatatcaa  37740
taacaaaggt aataatagta tcatcaacac caatgactaa gccctaagtg tatggtgcta  37800
taccactggt atacaagcac aacaaacctt attgtatcaa gctttcattg ttgttttcat  37860
taaacaaaaa caaaaaagaa aataaaatta aatataaata aaacttttca taacaaataa  37920
aatttcataa ttaaaaatat tttttcgttc attaaaattt aaaaagaaaa taaaattttt  37980
attgacaaaa aaatttttct gtggacgacc cccccactgt tattttaagc gctaccccca  38040
gccgccgccg caagcccccc ctaccccccc acgcagtttc aaaaaccaaa catgaatttt  38100
tatacatttt tatgtatatt ttgcatgtga aaaacgaact taaaatttca caatcgagct  38160
atcgttcgct catttttttac gttttttcac aatcaaaaat caaaaattca caatgatttt  38220
gaaaccgcgt ggttagaaac cctgttaaat caacgtttat gcagtctatg tataattcaa  38280
atttcacaag tgaatatttt tttcacaaat gaatatttca tattttgtga aaatgtataa  38340
aagtttgtga aatgtataaa tgaatataca ttattgaaaa ctgcatatac agttttatgc  38400
atttttcaaa gaacaagtaa aaaacaaaag tcaacacttt tgtttaactt ttttatactt  38460
ttcattaaac cataagacct aaaaaaagtc aaacttttttt atgatataat aatgcaaggt  38520
gataaaatga taagaaatga aaatgcgaaa aatggaatct ttctagcgtc acctaatgaa  38580
ttgaatttga caaaggaatc ggactatacc aataatatag atttgcactg gctacaaaaa  38640
```

-continued

```
ttaatattaa atgagagtat tattagtttt tattcatctt caatgtggcg acaagttaga  38700
gaactggtta gacaacgaga ccacaacgaa tgccaacggt gtgcttatta taaacgtctc  38760
acagtatcaa tgagacctaa agacttacat gttcaccata tagcagaatt agagaagttt  38820
ccagaactgg ctttaaacat gaataatctt atattggttt gccaccaatg tcacaacgaa  38880
attcacgaaa gattccaaga acaacagctt gatgttactg tttatgaaaa ctttgacgcc  38940
agcgaatggt ggtgttaaaa tgatatctga aaggtaaata tcaaaaagct ggtggttata  39000
cttttgaata tgttgaggag tgttaaaatg aaactgaacg gcgtagaata cgaaaatcca  39060
gaagcaattt tagaagtaag acaatacagt gacaaaagaa acaagctcat acaagatttg  39120
tatagacact atgtttcatt acgatatatt gcacgtggta atggttgtaa taaagctagt  39180
tttagtgtag tgtatgatga gttacaaaaa gaatacgttt tcaaagaagt tcaaagcgtt  39240
ttcaattata ataaagaaga aatgaataga cggcttgaat tatgtcgtaa atatattcca  39300
atgattgact aaaaggacgt gttagaaatg aatgaagata ttaacggtat caaaattaca  39360
gtagaagatt ttaggctaga atgcttggaa gcattgcaag ataaaggtaa attgaataca  39420
attagtaccg tattagtaaa taatattgct gcattgtatg aaaccgcctt aaaatgtcgt  39480
gaaaacattc ttgaaaacgg tgtaatgatt actacaattg gttcaactgg tcaaccaatc  39540
actaagaaaa atgaagctgt accattacaa gaaaagaata ttgcaacaat ggctaaatta  39600
ttgggtcaat tagaattaga taatattgta actaaggttg aaagcgcttt ttaatgagta  39660
catttcataa aataagctgg tttaagaaag aacatgagat tttgacccac tcaaaagata  39720
ttcttgattt accagcagta tctaattaca ttaatgctat tgatagcggt ttacagccag  39780
taagtgatga ggttgacaaa ttagttaaca acgtattacc aatggttctt gacatggttg  39840
ataatggtga agtatattta gatttaacaa tggtacaaca agtaatagct gtaccagcca  39900
acgcctttcc atatgggtta tatgattggg aagcatttct aactattttt atggttggtt  39960
ttagattttc agatgatgat acactttgct atgatgaata tttactttat atggcacgtg  40020
gtgctggtaa aaacggttac atgtcatgga tgatttttttc attattaagt aaaatcaacg  40080
gtattcctca ctatgatgta gctgtttcag caagtgcaga acgacaagct aaaacatcat  40140
ttactgatat ctttaatgta ctggctgaaa cagaccctga acaacgtgtt tttagacgta  40200
caaaaacaga aattgaacat agagaaacaa aatcagtgtt ccaatttcta tcaagcaatg  40260
ccacaacggc tgatggttta cgtttaggag ctttatattt agatgaaatc catgctattg  40320
atagttatga catgttaaac gtacttaaat catcactagg gaagattcca gacgctcgta  40380
tattcattac aaccacagat ggttatacac gtggtagtgt tttagacagc tacaaagaac  40440
aaggtagaca agttttagat ggtgaactag gtattaacta ccctaaagat gatttaaaac  40500
acagtaggct gttaccattc atgtgttgta tcaatgattt aagtgaagca aaagacgaac  40560
aaggttggta taaagccaat ccatcattaa ggtttaataa acaattatta caacaatata  40620
gaaaagaagt cattcaaatt gaccgtaatg ccgaacttaa cattgagttt catgttaagc  40680
gtgtgaacta tccaaaagaa gataatcgct ttgcactggc tacacgtgaa gaattagaag  40740
ctaccaaaga aaaatgtttg gctgattatg tggaagaata cggcgacaat gaagtttatg  40800
gttgtgttga ctggtctaac acacgagatt taaccagtgt agggctaatt gcacacgacc  40860
aattacacga ccgctatttt tacgaacatg aaagctttat cactcataac gagtacacaa  40920
atggacaaat aaatcctaaa gtactacaag ctggcaaaga ttctggtaaa ttaaacgttg  40980
```

-continued

```
tttatacaaa agatattgaa gaacgttatg tagtagacta ttttgtgaaa atgagtgaac  41040
gatactatat taacaaaata tttattgacc aatttaagag tactttactt aaaccagcgc  41100
ttgaaaaagc tggatttgaa gttgttgtag taccagtaaa aatggtaact gaaacaatga  41160
tcgcaccaca aatagataaa atgtttgcac aaggtaatat gtttgctggt aatgacccct  41220
tatttacgtg ggctatgaac aatttacaaa aagatattac taaaaatggt gttagattta  41280
ttaaaattga accaaaagca cgtaaaacag acccagccag cgcttttatc tctggtttaa  41340
ttggtttatt agacaatgaa ccagaccacc aagacggctt tataggtaag tttattggtt  41400
aaatatacat tgataagacc tttaaggagg tcttattttt gtgatataat ggtgtgtagt  41460
attatgaagg gggtgcagaa tgagtattat ttctgatttt ctaggctttt ctagtgaaat  41520
gatgaatgac ggcacaggaa acattattga tttaaatgat ttttgttata acgtagaagt  41580
tgcttcatat cacagattgg ctatagaaat agcaatagat ttaattggta atgccgttgc  41640
tagggttgat tggaatgtat tcaaaaagaa tattttacaa caaaacatag taacaactac  41700
gttaaacggt caaccaaacg cattacaaac atctagcgag ttctttaagc tcatgacacg  41760
caaattactg ttacgtggtg aagttcttat tgttgaaatt aacaatgaat tgtttgtagc  41820
tgattgttat gaaagcgaac aaactaagta taatgaagtg acatatagtg atattcaaat  41880
taatggtaaa gacacaccta aaaagaaata caaaaacaat gaagtaatct tcatgaaata  41940
tggtgataca gttctagctg catacttaga aagttatatg caattaatga acccattaac  42000
aagtagcgct gtagaaagtt tcaagtcaaa ccgtacaagg cgttttgtga ttagttctga  42060
tgattatagg gctaacttaa cagaagtgca agaaaacttt aataaaatga tggaacaaca  42120
gttagcttca ttcattggct caaagaaagc tacagcaatc tatgccaaac ctaaaaagaa  42180
tgatttgatt gatatgtctg ataaaaactt tatgatgagt acagacgcta gaggtttaat  42240
tagtgacacg tttaaaaccg ttgcaaacgc ttttcatatt ccaccagaat acatgctagg  42300
tggtgcatta tctcaaatga ttgttgataa ctttcttgta aacgctgtat atcctattgt  42360
tgacatgttt aaagaagcat ttaacaattt ccaatacagc caactag                42407
```

*ENTEROCOCCUS FAECIUM* BACTERIOPHAGE ENT-FAP-4 AND USE FOR INHIBITING *ENTEROCOCCUS FAECIUM* PROLIFERATION OF SAME

CROSS-REFERENCE TO RELATED APPLICATIONS

This application is a U.S. National Phase Application of International Application No. PCT/KR2018/000509, filed Jan. 11, 2018, which claims priority to Korean Application No. 10-2017-0023319, filed Feb. 22, 2017, each of which are hereby incorporated by reference in their entirety.

The Sequence Listing submitted Aug. 21, 2019, as a text file named "08162_0059U1_Sequence_Listing.txt," created on Jul. 26, 2019, and having a size of 54,220 bytes is hereby incorporated by reference pursuant to 37 C.F.R. § 1.52(e)(5).

TECHNICAL FIELD

The present invention relates to a bacteriophage isolated from nature, which infects Enterococcus faecium to thus kill *Enterococcus faecium*, and a method of preventing or treating an *Enterococcus faecium* infection using a composition containing the above bacteriophage as an active ingredient. More particularly, the present invention relates to a Siphoviridae bacteriophage Ent-FAP-4 (Accession number: KCTC 12854BP) isolated from nature, which has the ability to kill *Enterococcus faecium* and has the genome represented by SEQ ID NO: 1, and a method of preventing or treating an *Enterococcus faecium* infection using a composition containing the above bacteriophage as an active ingredient.

BACKGROUND ART

*Enterococcus* is a facultative anaerobic gram-positive coccus that is present in the gastrointestinal tract and in the urogenital system. The *Enterococcus* genus has been reported to have about 19 species, including *Enterococcus faecalis, Enterococcus faecium, Enterococcus durans*, and *Enterococcus casseliflavus*. Among these, *Enterococcus faecalis* and *Enterococcus pseudomonas* are considered to be the main bacterial species causing actual infections. In the past, infections caused by Enterococcus faecalis were very common, but the incidence of infections caused by *Enterococcus faecium* has increased recently.

*Enterococcus* has comparatively low toxicity and does not cause diseases in healthy people, but induces a variety of opportunistic infections such as urinary tract infection, wound infection, bacteremia, endocarditis and the like in elderly people, immunocompromised patients, patients with chronic underlying diseases, or hospitalized patients. Furthermore, *Enterococcus* may acquire a virulence factor through gene hybridization from the outside to thus induce an infectious disease. Among infections caused by *Enterococcus*, urinary tract infection is the most frequent, followed by wound infection. Other major infections by *Enterococcus* may include endocarditis, 5 to 20% of bacterial endocarditis being caused by *Enterococcus.*

Meanwhile, *Enterococcus* is resistant to many antibiotics including penicillin, cephalosporins, etc. and thus the problem therewith is even more serious. *Enterococcus* is known to obtain new DNA (plasmids or transposons) or to obtain antibiotic resistance using mutations. In particular, *Enterococcus*, which has acquired resistance to aminoglycosides, cannot be killed if it causes endocarditis or serious infection, making it difficult to successfully treat the same. It is reported that the mortality rate is 67% in the case of bacteremia due to vancomycin-resistance enterococci (VRE).

In the *Enterococcus* genus, *Enterococcus faecium* is known to have a relatively high antibiotic resistance rate compared to other *Enterococcus* species, and thus the clinical significance thereof is receiving attention. Hence, the development of drugs for use in the prevention or treatment of infection with antibiotic-resistant *Enterococcus faecium* is urgently required.

Recently, the use of bacteriophages as a countermeasure against infectious bacterial diseases has attracted considerable attention. In particular, these bacteriophages are receiving great attention due to strong antibacterial activity against antibiotic-resistant bacteria. Bacteriophages are very small microorganisms infecting bacteria, and are usually simply called "phages". Once a bacteriophage infects a bacterium, the bacteriophage is proliferated inside the bacterial cell. After proliferation, the progeny of the bacteriophage destroy the bacterial cell wall and escape from the host bacteria, demonstrating that the bacteriophage has the ability to kill bacteria. The manner in which the bacteriophage infects bacteria is characterized by very high specificity thereof, and thus the range of types of bacteriophages infecting a specific bacterium is limited. That is, a certain bacteriophage may infect only a specific bacterium, suggesting that a certain bacteriophage is capable of providing an antibacterial effect only for a specific bacterium and thus is capable of killing the specific bacterium alone without harming other bacteria. Due to this bacteria specificity of bacteriophages, the bacteriophage confers antibacterial effects only upon target bacteria, but does not affect commensal bacteria in the environment or in the intestines of animals. Conventional antibiotics, which have been widely used for bacterial treatment, concurrently influence many other kinds of bacteria. This causes problems such as environmental pollution and the disturbance of normal flora in animals. In contrast, the use of bacteriophages does not disturb normal flora in animals, because the target bacterium is selectively killed. Hence, bacteriophages may be utilized safely, which thus greatly lessens the probability of adverse effects of use thereof compared to antibiotics.

Bacteriophages were first discovered by the English bacteriologist Twort in 1915 when he noticed that *Micrococcus* colonies softened and became transparent due to something unknown. In 1917, the French bacteriologist d'Herelle discovered that *Shigella dysenteriae* in the filtrate of dysentery patient feces was destroyed by something, and further studied this phenomenon. As a result, he independently identified bacteriophages, and named them bacteriophages, which means "eater of bacteria". Since then, bacteriophages acting against such pathogenic bacteria as *Shigella, Salmonella Typhi*, and *Vibrio cholerae* have been continually identified.

Owing to the unique ability of bacteriophages to kill bacteria, bacteriophages have attracted attention as a potentially effective countermeasure against bacterial infection since their discovery, and a lot of research related thereto has been conducted. However, since penicillin was discovered by Fleming, studies on bacteriophages have continued only in some Eastern European countries and the former Soviet Union, because the spread of antibiotics was generalized. Since 2000, the limitations of conventional antibiotics have become apparent due to the increase in antibiotic-resistant bacteria, and the possibility of developing bacteriophages as a substitute for conventional antibiotics has been highlighted, and thus bacteriophages are again attracting attention as antibacterial agents.

As demonstrated above, bacteriophages tend to be highly specific for target bacteria. Because of this specificity, bacteriophages frequently exhibit an antibacterial effect only for certain strains of bacteria, even within the same species. In addition, the antibacterial strength of bacteriophages may vary depending on the target bacterial strain. Therefore, it is necessary to collect many kinds of bacteriophages that are useful in order to effectively control specific bacteria. Hence, in order to develop an effective bacteriophage utilization method for controlling *Enterococcus faecium*, many kinds of bacteriophages that exhibit antibacterial action against *Enterococcus faecium* must be acquired. Furthermore, the resulting bacteriophages need to be screened as to whether or not they are superior to others in view of the aspect of antibacterial strength and spectrum.

DISCLOSURE

Technical Problem

Therefore, the present inventors endeavored to develop a pharmaceutical composition applicable for the prevention or treatment of an *Enterococcus faecium* infection using a bacteriophage that is isolated from nature and is capable of killing *Enterococcus faecium*, and further to establish a method of preventing or treating an Enterococcus faecium infection using the pharmaceutical composition. As a result, the present inventors isolated a bacteriophage suitable for this purpose from nature and determined the gene sequence of the genome, which distinguishes the isolated bacteriophage from other bacteriophages. Then, the present inventors developed a pharmaceutical composition containing the bacteriophage as an active ingredient, and ascertained that this pharmaceutical composition is capable of being used to effectively prevent or treat an *Enterococcus faecium* infection, thus culminating in the present invention.

Accordingly, it is an object of the present invention to provide a Siphoviridae bacteriophage Ent-FAP-4 (Accession number: KCTC 12854BP) isolated from nature, which has the ability to kill *Enterococcus faecium* and has the genome represented by SEQ ID NO: 1.

It is another object of the present invention to provide a pharmaceutical composition applicable for preventing an *Enterococcus faecium* infection, which contains, as an active ingredient, an isolated bacteriophage Ent-FAP-4 (Accession number: KCTC 12854BP) infecting *Enterococcus faecium* to thus kill *Enterococcus faecium.*

It is another object of the present invention to provide a method of preventing an *Enterococcus faecium* infection using the pharmaceutical composition applicable for preventing an *Enterococcus faecium* infection, which contains, as an active ingredient, the isolated bacteriophage Ent-FAP-4 (Accession number: KCTC 12854BP) infecting *Enterococcus faecium* to thus kill *Enterococcus faecium.*

It is another object of the present invention to provide a pharmaceutical composition applicable for treating an *Enterococcus faecium* infection, which contains, as an active ingredient, the isolated bacteriophage Ent-FAP-4 (Accession number: KCTC 12854BP) infecting *Enterococcus faecium* to thus kill *Enterococcus faecium.*

It is another object of the present invention to provide a method of treating an *Enterococcus faecium* infection using the pharmaceutical composition applicable for treating an *Enterococcus faecium* infection, which contains, as an active ingredient, the isolated bacteriophage Ent-FAP-4 (Accession number: KCTC 12854BP) infecting *Enterococcus faecium* to thus kill *Enterococcus faecium.*

It is another object of the present invention to provide a disinfectant, which contains, as an active ingredient, the isolated bacteriophage Ent-FAP-4 (Accession number: KCTC 12854BP) infecting *Enterococcus faecium* to thus kill *Enterococcus faecium*. In particular, this disinfectant is effective at preventing infection in a hospital.

It is another object of the present invention to provide an antibiotic, which contains, as an active ingredient, the isolated bacteriophage Ent-FAP-4 (Accession number: KCTC 12854BP) infecting *Enterococcus faecium* to thus kill *Enterococcus faecium.*

Technical Solution

The present invention provides a Siphoviridae bacteriophage Ent-FAP-4 (Accession number: KCTC 12854BP) isolated from nature, which has the ability to kill *Enterococcus faecium* and has the genome represented by SEQ ID NO: 1, a pharmaceutical composition containing the Siphoviridae bacteriophage Ent-FAP-4 as an active ingredient, and a method of preventing or treating an *Enterococcus faecium* infection using the pharmaceutical composition.

The bacteriophage Ent-FAP-4 was isolated by the present inventors and then deposited at Korean Collection for Type Cultures, Korea Research Institute of Bioscience and Biotechnology on Jun. 23, 2015 (Accession number: KCTC 12854BP).

The present invention also provides a pharmaceutical composition applicable for the prevention or treatment of an *Enterococcus faecium* infection, which contains the bacteriophage Ent-FAP-4 as an active ingredient. Examples of the pharmaceutical composition include, but are not limited to, disinfectants or antibiotics.

Since the bacteriophage Ent-FAP-4 contained in the pharmaceutical composition of the present invention kills *Enterococcus faecium* effectively, it is effective in the prevention (prevention of infection) or treatment (treatment of infection) of diseases, such as urinary tract infection, wound infection, bacteremia, endocarditis and the like, caused by *Enterococcus faecium*. Therefore, the composition of the present invention is capable of being utilized for the prevention or treatment of diseases caused by *Enterococcus faecium*. In the present invention, diseases caused by *Enterococcus faecium* may include urinary tract infections, wound infections, bacteremia, endocarditis, and the like.

*Enterococcus faecium* in this specification may be sensitive to existing antibiotics or may be resistant to existing antibiotics. Briefly, it does not matter whether or not resistance to existing antibiotics is exhibited.

As used herein, the terms "prevention" and "prevent" refer to (i) prevention of an *Enterococcus faecium* infection and (ii) inhibition of the development of diseases caused by an *Enterococcus faecium* infection.

As used herein, the terms "treatment" and "treat" refer to all actions that (i) suppress diseases caused by *Enterococcus faecium* and (ii) alleviate the pathological condition of the diseases caused by *Enterococcus faecium.*

As used herein, the terms "isolate", "isolating", and "isolated" refer to actions that isolate bacteriophages from nature by using diverse experimental techniques and that secure characteristics that can distinguish the bacteriophage of the present invention from others, and further include the action of proliferating the bacteriophage of the present invention using bioengineering techniques so that the bacteriophage is industrially applicable.

The pharmaceutically acceptable carrier included in the pharmaceutical composition of the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The pharmaceutical composition of the present invention may additionally include lubricants, wetting agents, sweeteners, flavors, emulsifiers, suspension agents, and preservatives, in addition to the above ingredients.

The pharmaceutical composition of the present invention may be used through spreading or spraying on a diseased site, or may be administered through oral administration or parenteral administration. Here, the parenteral administration may include intravenous administration, intraperitoneal administration, intramuscular administration, subcutaneous administration or local administration.

The appropriate spread, spray and dose of the pharmaceutical composition of the present invention may vary depending on factors such as the formulation method, the mode of administration, the age, weight, gender and diseased condition of the subject animal or patient, diet, administration time, administration route, excretion rate, and responsiveness. Usually, a dose effective for the desired treatment may be easily determined and prescribed by skilled physicians or veterinarians.

The bacteriophage Ent-FAP-4 is contained as an active ingredient in the pharmaceutical composition of the present invention. The bacteriophage Ent-FAP-4 is contained at a concentration of $1\times10^{1}$ pfu/ml to $1\times10^{3°}$ pfu/ml or $1\times10^{1}$ pfu/g to $1\times10^{30}$ pfu/g, and preferably at a concentration of $1\times10^{4}$ pfu/ml to $1\times10^{15}$ pfu/ml or $1\times10^{4}$ pfu/g to $1\times10^{15}$ pfu/g.

The pharmaceutical composition of the present invention may be formulated using a pharmaceutically acceptable carrier and/or excipient in accordance with a method that may be easily carried out by those skilled in the art to which the present invention belongs in order to prepare the same in a unit dosage form or insert the same into a multi-dose container. Here, the formulation thereof may be provided in the form of a solution, a suspension, or an emulsion in an oil or aqueous medium, or in the form of an extract, a powder, a granule, a tablet, or a capsule, and may additionally contain a dispersant or a stabilizer.

The pharmaceutical composition of the present invention may be prepared as a disinfectant or an antibiotic depending on the purpose of use thereof, without limitation thereto. As used herein, the term "antibiotic" collectively refers to preservatives, bactericides and antibacterial agents.

In order to improve the effectiveness thereof, bacteriophages that confer antibacterial activity against other bacterial species may be further included in the pharmaceutical composition of the present invention. In addition, other kinds of bacteriophages that have antibacterial activity against *Enterococcus faecium* may be further included in the pharmaceutical composition of the present invention. These bacteriophages may be combined appropriately so as to maximize the antibacterial effects thereof, because their antibacterial activities against *Enterococcus faecium* may vary from the aspects of antibacterial strength and spectrum.

Advantageous Effects

According to the present invention, the method of preventing or treating an *Enterococcus faecium* infection using the pharmaceutical composition containing the bacteriophage Ent-FAP-4 as an active ingredient can have the advantage of very high specificity for *Enterococcus faecium*, compared to conventional methods based on existing antibiotics. This means that the composition can be used for preventing or treating an *Enterococcus faecium* infection without affecting other bacteria, namely useful commensal bacteria, and has fewer side effects attributable to the use thereof. Typically, when antibiotics are used, commensal bacteria are also damaged, thus entailing various side effects owing to the use thereof. Meanwhile, in the case of various bacteriophages exhibiting antibacterial activity against the same species of bacteria, the antibacterial activities of the bacteriophages are different with regard to antibacterial strength and spectrum [the spectrum of the antibacterial activity of the bacteriophages applied to individual bacteria strains in terms of the strains of various bacteria belonging to *Enterococcus faecium*, bacteriophages usually being effective only on some bacterial strains, even within the same species, and the antibacterial activity of bacteriophages thus depending on the bacterial strain even for the same species of bacteria]. Accordingly, the present invention can provide antibacterial activity against *Enterococcus faecium* discriminating from that of other bacteriophages acting on *Enterococcus faecium*. This provides a great variety of applicability to industrial fields.

DESCRIPTION OF DRAWINGS

FIG. 1 is an electron micrograph showing the morphology of the bacteriophage Ent-FAP-4.

FIG. 2 is a photograph showing the results of an experiment on the ability of the bacteriophage Ent-FAP-4 to kill *Enterococcus faecium*, in which the clear zone is a plaque formed by lysis of the bacteria.

MODE FOR INVENTION

Hereinafter, the present invention will be described in more detail with reference to Examples. However, the Examples are merely examples of the present invention, and the scope of the present invention is not limited to the Examples.

Example 1: Isolation of Bacteriophage Capable of Killing *Enterococcus faecium*

Samples were collected from nature to isolate the bacteriophage capable of killing *Enterococcus faecium*. Here, the *Enterococcus faecium* used for the bacteriophage isolation had been previously isolated and identified as *Enterococcus faecium* by the present inventors.

The procedure for isolating the bacteriophage is described in detail hereinafter. The collected sample was added to a TSB (Tryptic Soy Broth) culture medium (casein digest, 17 g/L; soybean digest, 3 g/L; dextrose, 2.5 g/L; NaCl, 5 g/L; dipotassium phosphate, 2.5 g/L) inoculated with *Enterococcus faecium* at a ratio of 1/1000, followed by shaking culture at 37° C. for 3 to 4 hr. Upon completion of the culture, centrifugation was performed at 8,000 rpm for 20 min and a supernatant was recovered. The recovered supernatant was inoculated with *Enterococcus faecium* at a ratio of 1/1000, followed by shaking culture at 37° C. for 3 to 4 hr. When the sample contained the bacteriophage, the above procedure was repeated a total of 5 times in order to sufficiently increase the number (titer) of bacteriophages. After repeating the procedure 5 times, the culture broth was subjected to centrifugation at 8,000 rpm for 20 min. After centrifugation, the recovered supernatant was filtered using a 0.45 μm filter. The obtained filtrate was used in a typical spot assay for examining whether or not a bacteriophage capable of killing *Enterococcus faecium* was included therein.

The spot assay was performed as follows: TSB culture medium was inoculated with *Enterococcus faecium* at a ratio of 1/1000, followed by shaking culture at 37° C. overnight. 3 ml ($OD_{600}$ of 1.5) of the culture broth of *Enterococcus faecium* prepared above was spread on a TSA (Tryptic Soy Agar: casein digest, 15 g/L; soybean digest, 5 g/L; NaCl, 5 g/L; agar, 15 g/L) plate culture medium. The spread plate culture medium was left on a clean bench for about 30 min to thus dry the spread solution. After drying, 10 μl of the prepared filtrate was spotted onto the plate culture medium on which *Enterococcus faecium* was spread and then left to dry for about 30 min. After drying, the plate culture medium that was subjected to spotting was cultured without shaking at 37° C. for one day, and then examined for the formation of clear zones at the positions where the filtrate was dropped. In the case in which the filtrate generated a clear zone, it was judged that the bacteriophage capable of killing *Enterococcus faecium* was included therein. Through the above examination, it was possible to obtain a filtrate containing the bacteriophage having the ability to kill *Enterococcus faecium*.

The pure bacteriophage was isolated from the filtrate confirmed above to have the bacteriophage capable of killing *Enterococcus faecium*. A conventional plaque assay was used to isolate the pure bacteriophage. In detail, a plaque formed in the course of the plaque assay was recovered using a sterilized tip, which was then added to the culture broth of *Enterococcus faecium*, followed by culturing at 37° C. for 4 to 5 hr. After the culturing, centrifugation was performed at 8,000 rpm for 20 min to obtain a supernatant. The *Enterococcus faecium* culture broth was added to the obtained supernatant at a volume ratio of 1/50, followed by culturing at 37° C. for 4 to 5 hr. In order to increase the number of bacteriophages, the above procedure was repeated at least 5 times. Then, centrifugation was performed at 8,000 rpm for 20 min in order to obtain the final supernatant. A plaque assay was further performed using the resulting supernatant. In general, the isolation of a pure bacteriophage is not completed through a single iteration of a procedure, so the above procedure was repeated using the resulting plaque formed above. After at least 5 repetitions of the procedure, the solution containing the pure bacteriophage was obtained. The procedure for isolating the pure bacteriophage was repeated in its entirety until the generated plaques became similar to each other with respect to size and morphology. In addition, final isolation of the pure bacteriophage was confirmed using electron microscopy. The above procedure was repeated until the isolation of the pure bacteriophage was confirmed using electron microscopy. The electron microscopy was performed according to a conventional method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics thereof, the novel bacteriophage that was isolated above was confirmed to be a Siphoviridae bacteriophage.

The solution containing the pure bacteriophage confirmed above was subjected to the following purification process. The *Enterococcus faecium* culture broth was added to the solution containing the pure bacteriophage at a volume ratio of 1/50 based on the total volume of the bacteriophage solution, followed by further culturing for 4 to 5 hr. After the culturing, centrifugation was performed at 8,000 rpm for 20 min to obtain a supernatant. This procedure was repeated a total of 5 times in order to obtain a solution containing a sufficient number of bacteriophages. The supernatant obtained from the final centrifugation was filtered using a 0.45 μm filter, followed by a conventional polyethylene glycol (PEG) precipitation process. Specifically, PEG and NaCl were added to 100 ml of the filtrate reaching 10% PEG 8000/0.5 M NaCl, which was then left at 4° C. for 2 to 3 hr. Thereafter, centrifugation was performed at 8,000 rpm for 30 min to obtain the bacteriophage precipitate. The resulting bacteriophage precipitate was suspended in 5 ml of a buffer (10 mM Tris-HCl, 10 mM $MgSO_4$, 0.1% gelatin, pH 8.0). The resulting material may be referred to as a bacteriophage suspension or bacteriophage solution.

As a result, the pure bacteriophage purified above was collected, was named the bacteriophage Ent-FAP-4, and deposited at the Korean Collection for Type Cultures, Korea Research Institute of Bioscience and Biotechnology on Jun. 23, 2015 (Accession number: KCTC 12854BP).

Example 2: Separation and Sequence Analysis of Genome of Bacteriophage Ent-FAP-4

The genome of the bacteriophage Ent-FAP-4 was separated as follows. The genome was separated from the bacteriophage suspension obtained using the same method as in Example 1. First, in order to eliminate DNA and RNA of *Enterococcus faecium* included in the suspension, 200 U of each of DNase I and RNase A was added to 10 ml of the bacteriophage suspension and then left at 37° C. for 30 min. After being left for 30 min, in order to stop the DNase I and RNase A activity, 500 μl of 0.5 M ethylenediaminetetraacetic acid (EDTA) was added thereto, and the resulting mixture was then left for 10 min. In addition, the resulting mixture was further left at 65° C. for 10 min, and 100 μl of proteinase K (20 mg/ml) was then added thereto so as to break the outer wall of the bacteriophage, followed by reacting at 37° C. for 20 min. Thereafter, 500 μl of 10% sodium dodecyl sulfate (SDS) was added thereto, followed by reacting at 65° C. for 1 hr. After reaction for 1 hr, 10 ml of the solution of phenol:chloroform:isoamyl alcohol, mixed at a component ratio of 25:24:1, was added to the reaction solution, followed by mixing thoroughly. In addition, the resulting mixture was subjected to centrifugation at 13,000 rpm for 15 min to thus separate layers. Among the separated layers, the upper layer was selected, and isopropyl alcohol was added thereto at a volume ratio of 1.5, followed by centrifugation at 13,000 rpm for 10 min in order to precipitate the genome. After the precipitate was recovered, 70% ethanol was added to the precipitate, followed by centrifugation at 13,000 rpm for 10 min to wash the precipitate. The washed precipitate was recovered, vacuum-dried and then dissolved in 100 μl of water. This procedure was repeated to thus obtain a large amount of the genome of the bacteriophage Ent-FAP-4.

Information on the sequence of the genome of the bacteriophage Ent-FAP-4 obtained above was secured by performing next-generation sequencing analysis using an Illumina Mi-Seq apparatus provided by the National Instrumentation Center for Environmental Management, Seoul National University. The finally analyzed genome of the bacteriophage Ent-FAP-4 had a size of 42,407 bp, and the whole genome sequence is represented by SEQ ID NO: 1.

The homology (similarity) of the bacteriophage Ent-FAP-4 genomic sequence obtained above with previously reported bacteriophage genomic sequences was investigated using BLAST on the web. Based on the results of the BLAST investigation, there was no bacteriophage genomic sequence having a homology of 50% or more with the genomic sequence of the bacteriophage Ent-FAP-4.

Therefore, it can be concluded that the bacteriophage Ent-FAP-4 is a novel bacteriophage different from conventionally reported bacteriophages. Moreover, since the antibacterial strength and spectrum of bacteriophages typically depend on the type of bacteriophage, it is considered that the bacteriophage Ent-FAP-4 can provide antibacterial activity different from that of any other bacteriophages reported previously.

Example 3: Investigation of Killing Ability of Bacteriophage Ent-FAP-4 for *Enterococcus faecium*

The killing ability of the isolated bacteriophage Ent-FAP-4 for *Enterococcus faecium* was investigated. In order to evaluate the killing ability, the formation of clear zones was observed using a spot assay in the same manner as described in connection with Example 1. A total of 10 strains that had been isolated and identified as *Enterococcus faecium* by the present inventors were used as *Enterococcus faecium* for the investigation of killing ability. The bacteriophage Ent-FAP-4 had the ability to kill 9 strains, among 10 strains of *Enterococcus faecium*, that is, the experimental target. The representative experimental results thereof are shown in FIG. 2. Meanwhile, the ability of the bacteriophage Ent-FAP-4 to kill *Staphylococcus aureus, Pasteurella multocida, Clostridium perfringens, Lactobacillus plantarum, Streptococcus uberis* and *Pseudomonas aeruginosa* was also measured. Consequently, the bacteriophage Ent-FAP-4 was found not to have the ability to kill these microorganisms.

Therefore, it can be concluded that the bacteriophage Ent-FAP-4 has high ability to kill *Enterococcus faecium* and an antibacterial effect against many *Enterococcus faecium* bacteria, indicating that the bacteriophage Ent-FAP-4 can be used as an active ingredient of the composition for preventing or treating *Enterococcus faecium* infection.

Example 4: Experiment for Prevention of *Enterococcus faecium* Infection Using Bacteriophage Ent-FAP-4

100 μl of a bacteriophage Ent-FAP-4 solution at a level of $1\times10^9$ pfu/ml was added to a tube containing 9 ml of a TSB culture medium. To another tube containing 9 ml of a TSB culture medium, only the same amount of TSB culture medium was further added. An *Enterococcus faecium* culture broth was then added to each tube so that absorbance reached about 0.5 at 600 nm. After addition of *Enterococcus faecium*, the tubes were placed in an incubator at 37° C., followed by shaking culture, during which the growth of *Enterococcus faecium* was observed. As shown in Table 1 below, it was observed that the growth of *Enterococcus faecium* was inhibited in the tube to which the bacteriophage Ent-FAP-4 solution was added, whereas the growth of *Enterococcus faecium* was not inhibited in the tube to which the bacteriophage solution was not added.

TABLE 1

Growth inhibition of *Enterococcus faecium*

| Classification | $OD_{600}$ absorbance value 0 min after culture | 60 min after culture | 120 min after culture |
|---|---|---|---|
| Not added with bacteriophage solution | 0.5 | 0.9 | 1.6 |
| Added with bacteriophage solution | 0.5 | 0.4 | 0.3 |

The above results show that the bacteriophage Ent-FAP-4 of the present invention not only inhibits the growth of *Enterococcus faecium* but also has the ability to kill *Enterococcus faecium*. Therefore, it is concluded that the bacteriophage Ent-FAP-4 can be used as an active ingredient of the composition for preventing an Enterococcus faecium infection.

Example 5: Treatment 1 of Infectious Disease Caused by *Enterococcus faecium* Using Bacteriophage Ent-FAP-4

The therapeutic effect of the bacteriophage Ent-FAP-4 on animals afflicted with *Enterococcus faecium* was evaluated. 2 groups of forty 2-day-old chicks per group were prepared and reared separately, and the experiment was performed for 14 days. For 3 days from the fifth day after the start of the experiment, a feed containing $1\times10^7$ cfu/g of *Enterococcus faecium* was supplied in a typical feeding manner. From the last day of feeding with feed containing *Enterococcus faecium, Enterococcus faecium* was found in the feces of both groups. From the next day (the eighth day after the start of the experiment) after the supply of the feed including *Enterococcus faecium* for 3 days, a feed containing $1\times10^8$ pfu/g of bacteriophage Ent-FAP-4 was fed to chicks in the experimental group (administered with bacteriophage) in a typical feeding manner. In contrast, a feed having the same composition but excluding bacteriophage Ent-FAP-4 was fed to chicks in the control group (not administered with bacteriophage) in the same manner. From the ninth day after the start of the experiment, the number of *Enterococcus faecium* bacteria in the feces of the experimental animals was measured. An *Enterococcus-faecium*-selective medium (Pfizer Selective Enterococcus agar plate; MB cell) was used to prevent interference with other contaminating bacteria in the measurement of the number of *Enterococcus faecium* bacteria in this example. The sample was spread on the selective medium and cultured at 37° C. for 18 to 24 hr. Colonies presumed to be Enterococcus *faecium* were isolated from the selective medium, after which *Enterococcus faecium* was identified through polymerase chain reaction (PCR) (the case where the number of colonies identified as *Enterococcus faecium* through PCR is $10^2$ cfu/ml or more=2, the case where the number of colonies identified as *Enterococcus faecium* through PCR is $10^1$~$10^2$ cfu/ml=1, and the case where the number of colonies identified as *Enterococcus faecium* through PCR is $10^0$~$10^1$ cfu/ml=0). The results are shown in Table 2 below.

TABLE 2

| Results of measurement of number of *Enterococcus faecium* bacteria (mean) | | | | | | |
|---|---|---|---|---|---|---|
| Day | D9 | D10 | D11 | D12 | D13 | D14 |
| Control group (not administered with bacteriophage) | 1.0 | 1.0 | 1.1 | 1.2 | 1.1 | 1.3 |
| Experimental group (administered with bacteriophage) | 0.2 | 0.1 | 0.1 | 0 | 0 | 0 |

As is apparent from the above results, it can be concluded that the bacteriophage Ent-FAP-4 of the present invention is very effective in the treatment of diseases caused by Enterococcus faecium.

Example 6: Treatment 2 of Infectious Disease Caused by *Enterococcus faecium* Using Bacteriophage Ent-FAP-4

The therapeutic effect of the bacteriophage Ent-FAP-4 on diseases caused by *Enterococcus faecium* was evaluated as follows. 40 of 8-week-old mice were divided into a total of 2 groups of 20 mice per group, after which subgroups of 5 mice each were separately reared in individual experimental mouse cages, and the experiment was performed for 7 days. On the second day of the experiment, 0.1 ml of an *Enterococcus faecium* suspension was administered to all mice through intraperitoneal injection. The administered *Enterococcus faecium* suspension was prepared as follows. Specifically, *Enterococcus faecium* was cultured at 37° C. for 18 hr in a TSB medium, and only the cells were recovered, and the recovered cells were suspended in saline (pH 7.2) at a concentration of $5\times10^9$ cfu/ml. At 2 hr after administration of *Enterococcus faecium*, $10^9$ pfu of bacteriophage Ent-FAP-4 was administered through intraperitoneal injection to mice in the experimental group (administered with the bacteriophage solution). 0.1 ml of saline was administered through intraperitoneal injection to mice in the control group (not administered with the bacteriophage solution). Both the control and experimental groups were equally fed with feed and drinking water. Whether or not the mice survived was observed daily starting from the administration of *Enterococcus faecium* until the end of the test. The results are shown in Table 3 below.

TABLE 3

| Results of measurement of survival rate (%) | | | | | | |
|---|---|---|---|---|---|---|
| Day after bacteria administration | D0 | D1 | D2 | D3 | D4 | D5 |
| Control group (not administered with bacteriophage solution) | 100 | 75 | 30 | 10 | 10 | 10 |
| Experimental group (administered with bacteriophage solution through intraperitoneal injection) | 100 | 95 | 95 | 95 | 95 | 95 |

As is apparent from the above results, it can be concluded that the bacteriophage Ent-FAP-4 of the present invention is very effective in the treatment of diseases caused by *Enterococcus faecium.*

While the present invention has been particularly shown and described with reference to exemplary embodiments thereof, those skilled in the art will appreciate that the specific description is only a preferred embodiment, and that the scope of the present invention is not limited thereto. It is therefore intended that the scope of the present invention be defined by the claims appended hereto and their equivalents.

Accession Number

Name of Depositary Authority: KCTC
Accession number: KCTC 12854BP
Accession date: 20150623

The invention claimed is:

1. A method of suppressing diseases caused by a bacterial strain of *Enterococcus faecium* and alleviating pathological condition of the diseases caused by the bacterial strain of Enterococcus faecium, comprising: administering to an animal other than a human a composition comprising Siphoviridae bacteriophage Ent-FAP-4 which has an ability to specifically kill the bacterial strain of Enterococcus faecium and has the genome represented by the nucleic acid sequence of SEQ ID NO: 1, and is deposited as the accession number of KCTC 12854BP, wherein the diseases are urinary tract infections, wound infections, bacteremia or endocarditis.

* * * * *